(12) United States Patent
Corvera

(10) Patent No.: US 10,093,902 B2
(45) Date of Patent: Oct. 9, 2018

(54) HUMAN ADIPOSE TISSUE WHITE AND 'BROWN-ON-WHITE' PROGENITORS FOR RECONSTRUCTIVE AND METABOLIC THERAPIES

(71) Applicant: University of Massachusetts, Boston, MA (US)

(72) Inventor: Silvia Corvera, Westborough, MA (US)

(73) Assignee: University of Massachusetts, Boston, MA (US)

(*) Notice: Subject to any disclaimer, the term of this patent is extended or adjusted under 35 U.S.C. 154(b) by 485 days.

(21) Appl. No.: 14/660,381

(22) Filed: Mar. 17, 2015

(65) Prior Publication Data
US 2015/0259647 A1 Sep. 17, 2015

Related U.S. Application Data

(60) Provisional application No. 61/954,289, filed on Mar. 17, 2014.

(51) Int. Cl.
| C12N 5/077 | (2010.01) |
| C12N 5/071 | (2010.01) |
| A61K 35/28 | (2015.01) |

(52) U.S. Cl.
CPC ............ *C12N 5/0653* (2013.01); *A61K 35/28* (2013.01); *C12N 5/0692* (2013.01); *C12N 2501/105* (2013.01); *C12N 2501/11* (2013.01); *C12N 2501/115* (2013.01); *C12N 2501/119* (2013.01); *C12N 2501/165* (2013.01)

(58) Field of Classification Search
None
See application file for complete search history.

(56) References Cited

U.S. PATENT DOCUMENTS

2012/0308536 A1  12/2012  Hedrick et al.

FOREIGN PATENT DOCUMENTS

WO   WO 2014/026201   2/2014

OTHER PUBLICATIONS

International Search Report and the Written Opinion of the International Searching Authority issued in International Application No. PCT/US2015/021038 dated Jun. 18, 2015, 11 pgs.
Baer and Geiger, "Adipose-Derived Mesenchymal Stromal/Stem Cells: Tissue Localization, Characterization, and Heterogeneity", Stem Cells International, vol. 2012:812693 (2012).
Baker et al., "Use of the mouse aortic ring assay to study angiogenesis", Nature Protocols, vol. 7:89-104 (2012).
Benzinou et al., "Common nonsynonymous variants in PCK1 confer risk of obesity", Nature Genetics, vol. 40:943-945 (2008).
Blondin et al., "Increased Brown Adipose Tissue Oxidative Capacity in Cold-Acclimated Humans", J Clin Endocrinol Metab., vol. 99:E438-E446 (2014).
Bouloumie et al., "Angiogenesis in adipose tissue", Ann Endocrinol (Paris), vol. 63:91-95 (2002).
Boyd et al., "Human Embryonic Stem Cell-Derived Mesoderm-like Epithelium Transitions to Mesenchymal Progenitor Cells", Tissue Engineering: Part A, vol. 15:1897-1907 (Aug. 2009).
Brehm et al., "Engraftment of human HSCs in nonirradiated newborn NOD-*scid IL2rγ^null* mice is enhanced by transgenic expression of membrane-bound human SCF", Blood, vol. 119:2778-2788 (2012).
Brown et al., "Basic science review on adipose tissue for clinicians", Plast Reconstr Surg., vol. 126(6):1936-1946 (2010).
Cousin et al., "Occurrence of brown adipocytes in rat white adipose tissue: molecular and morphological characterization", Journal of Cell Science, vol. 103:931-942 (1992).
Cypess, et al., "Identification and Importance of Brown Adipose Tissue in Adult Humans", The New England Journal of Medicine, vol. 360:1509-1517 (2009).
Gealekman et al., "Depot-Specific Differences and Insufficient Subcutaneous Adipose Tissue Angiogenesis in Human Obesity", Circulation, vol. 123:186-194 (Jan. 3, 2011).
Gir et al., "Human adipose stem cells: current clinical applications", Plast Reconstr Surg., vol. 129(6):1277-1290 (Jun. 2012).
Gonzalez-Cruz et al., Cellular mechanical properties reflect the differentiation potential of adipose-derived mesenchymal stem cells, Proceedings of the National Academy of Sciences, vol. 109:1523-1529 (May 21, 2012).
Gupta et al., "Zfp423 Expression Identifies Commi8tted Preadipocytes and Localizes to Adipose Endothelial and Perivascular Cells", Cell Metabolism, vol. 15:230-239 (2012).
Han et al., "The spatiotemporal development of adipose tissue", Development, vol. 138:5027-5037 (2011).
Harms et al., "Brown and beige fat: development, function and therapeutic potential", Nat Med, vol. 19:1252-1263 (2013).
Hwang et al., "Adipocyte differentiation and leptin expression", Annu Rev Cell Dev Biol., vol. 13:231-259 (1997).
Jackson et al., "Obesity and impaired prohormone processing associated with mutations in the human prohormone convertase 1 gene", Nature Genetics, vol. 16:303-306 (1997).
Kawaguchi et al., "De novo adipogenesis in mice at the site of injection of basement membrane and basic fibroblast growth factor", Proc. Natl. Acad. Sci. USA, vol. 95:1062-1066 (1998).
Kim et al., "Homing of adipose-derived stem cells to radiofrequency catheter ablated canine atrium and differentiation into cardiomyocyte-like cells", Int. J. Cardiol., vol. 146(3):371-378 (2011).
Lee et al., "Stem Cell-Mediated Accelerated Bone Healing Observed with in Vivo Molecular and Small Animal Imaging Technologies in a Model of Skeletal Injury" J. Orthop. Res., vol. 27:295-302 (2009).
Lidell et al., "Two types of brown adipose tissue in humans", Adipocyte, vol. 3:63-66 (2014).
Marra and Rubin, "The potential of adipose-derived stem cells in craniofacial repair and regeneration", Birth Defects Res C Embryo Today, vol. 96:95-97 (2012).
Miller et al., "Interleukin-33 Induces Protective Effects in Adipose Tissue Inflammation During Obesity in Mice", Circ Res., vol. 107:650-658 (2010).
Mizuno et al., Concise Review: Adipose-Derived Stem Cells as a Novel Tool for Future Regenerative Medicine, Stem Cells, vol. 30:804-810 (2012).

(Continued)

*Primary Examiner* — Jennifer M. H. Tichy
(74) *Attorney, Agent, or Firm* — Fish & Richardson P.C.

(57) ABSTRACT

Methods for preparation of prospectively identified human adipose stem cells enriched populations thereof, e.g., for therapy.

7 Claims, 10 Drawing Sheets

(56) References Cited

OTHER PUBLICATIONS

Nedergaard et al., "Unexpected evidence for active brown adipose tissue in adult humans", Am J Physiol Endocrinol Metab., vol. 293: E444-E452 (2007).
Nishimura et al., "Adipogenesis in Obesity Requires Close Interplay Between Differentiating Adipocytes, Stromal Cells, and Blood Vessels", Diabetes, vol. 56(6):1517-1526 (2007).
Pisani et al., "Differentiation of Human Adipose-Derived Stem Cells into "Brite" (Brown-in White) Adipocytes", Frontiers in Endocrinology, vol. 2:1-9 (2011).
Rojas-Rodriguez et al., "Adipose Tissue Angiogenesis Assay", Methods Enzymol., vol. 537:75-91 (2014).
Sterodimas et al., "Tissue engineering with adipose-derived stem cells (ADSCs): current and future applications", J Plast Reconstr Aesthet Surg., vol. 63(11):1886-1892 (2010).
Tang et al., "Thiazolidinediones Regulate Adipose Lineage Dynamics", Cell Metabolism, vol. 14(1):116-122 (2011).
Tang et al., "White Fat Progenitors Reside in the Adipose Vasculature", Science, vol. 322(5901):583-586 (2008).
Tran and Kahn, "Transplantation of Adipose Tissue and Adipose-Derived Stem Cells as a Tool to Study Metabolic Physiology and for Treatment of Disease", Nature Reviews Endocrinology, vol. 6:195-213 (2010).
Tran et al., "The Vascular Endothelium of the Adipose Tissue Gives Rise to Both White and Brown Fat Cells", Cell Metabolism, vol. 15(2):222-229 (2012).
Van Marken Lichtenbelt et al., Cold-Activated Brown Adipose Tissue in Healthy Men, The New England Journal of Medicine, vol. 360:1500-1508 (2009).
Wang et al., "Brown Adipose Tissue in Humans is Activated by Elevated Plasma Catecholamines Levels and is Inversely Related to Central Obesity", PLoS One, vol. 6:e21006 (2011).
Wang et al., "The brown fat-enriched secreted factor Nrg4 preserves metabolic homeostasis through attenuating hepatic lipogenesis", Nat Med., vol. 20:1436-1443 (2014).
Wen et al., "Meta-analysis identifies common variants associated with body mass index in East Asians", Nature Genetics, vol. 44:307-311 (2012).
Yoshimura et al., "Adipose-derived stem/progenitor cells: roles in adipose tissue remodeling and potential use for soft tissue augmentation", Regen Med., vol. 4(2):265-273 (2009).
Yoshimura et al., "Cell-assisted lipotransfer for facial lipoatrophy: efficacy of clinical use of adipose-derived stem cells", Dermatol Surg., vol. 34(9):1178-1185 (2008).
Yoshimura et al., "Progenitor-enriched adipose tissue transplantation as rescue for breast implant complications", Breast J., vol. 16(2):169-175 (2010).
Zhang et al., "Regulation of adiponectin and leptin gene expression in white and brown adipose tissues: influence of beta3-adrenergic agonists, retinoic acid, leptin and fasting", Biochim Biophys Acta., vol. 1584:115-122 (2002).
Zimmerlin et al., "Mesenchymal markers on human adipose stem/progenitor cells", Cytometry A, vol. 83:134-140 (Jan. 1, 2013).

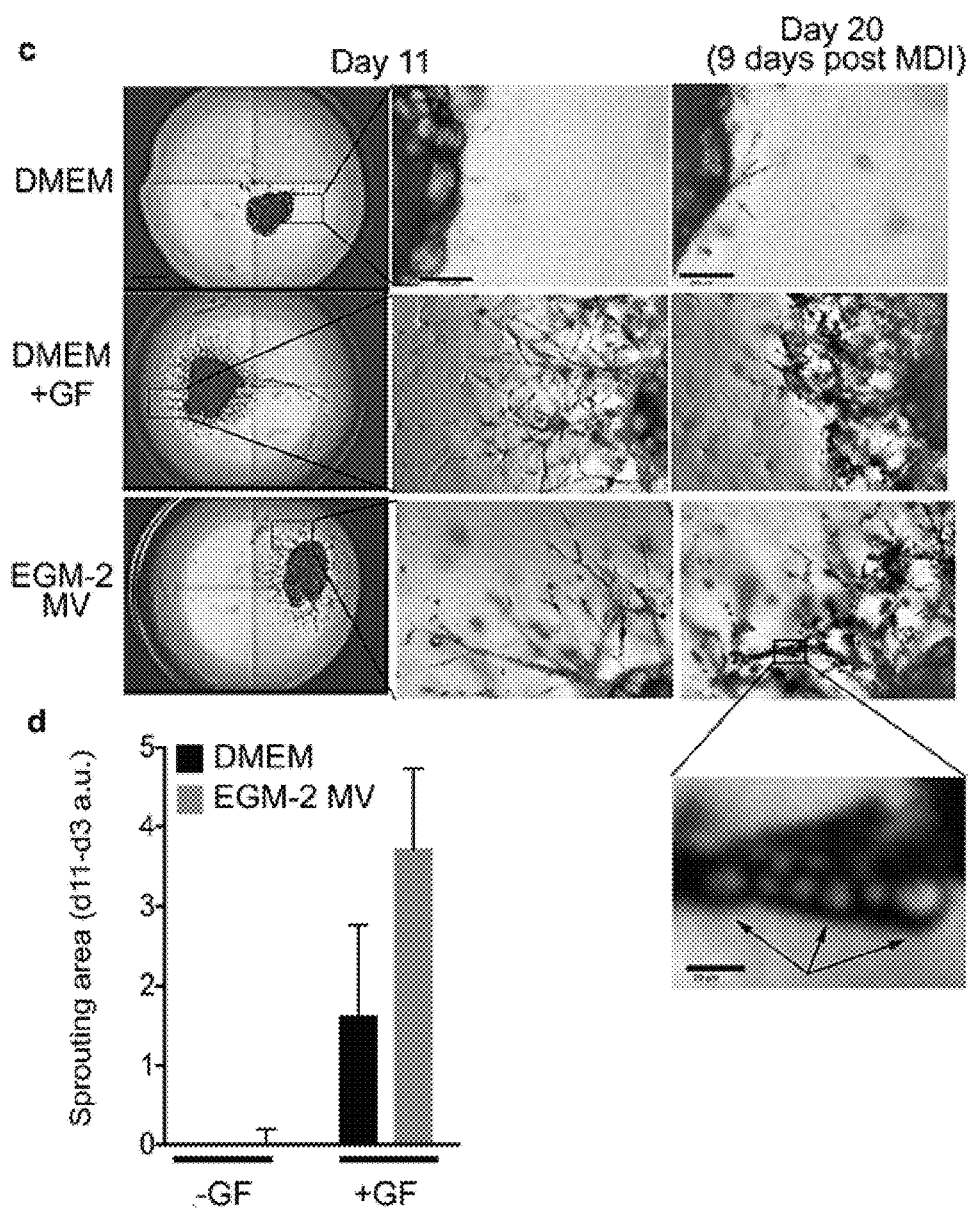
FIGURES 1C-D

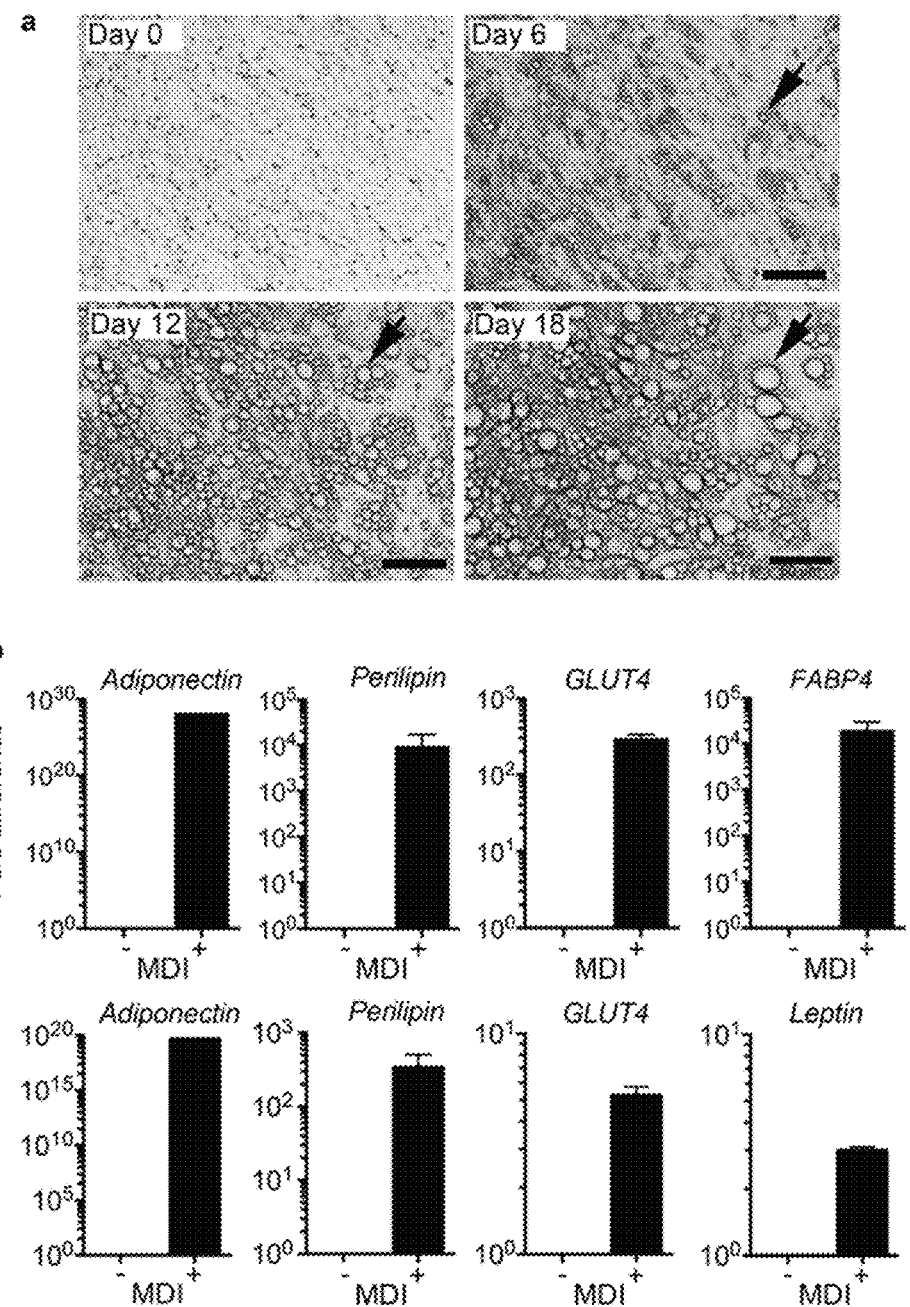
FIGURES 2A-C

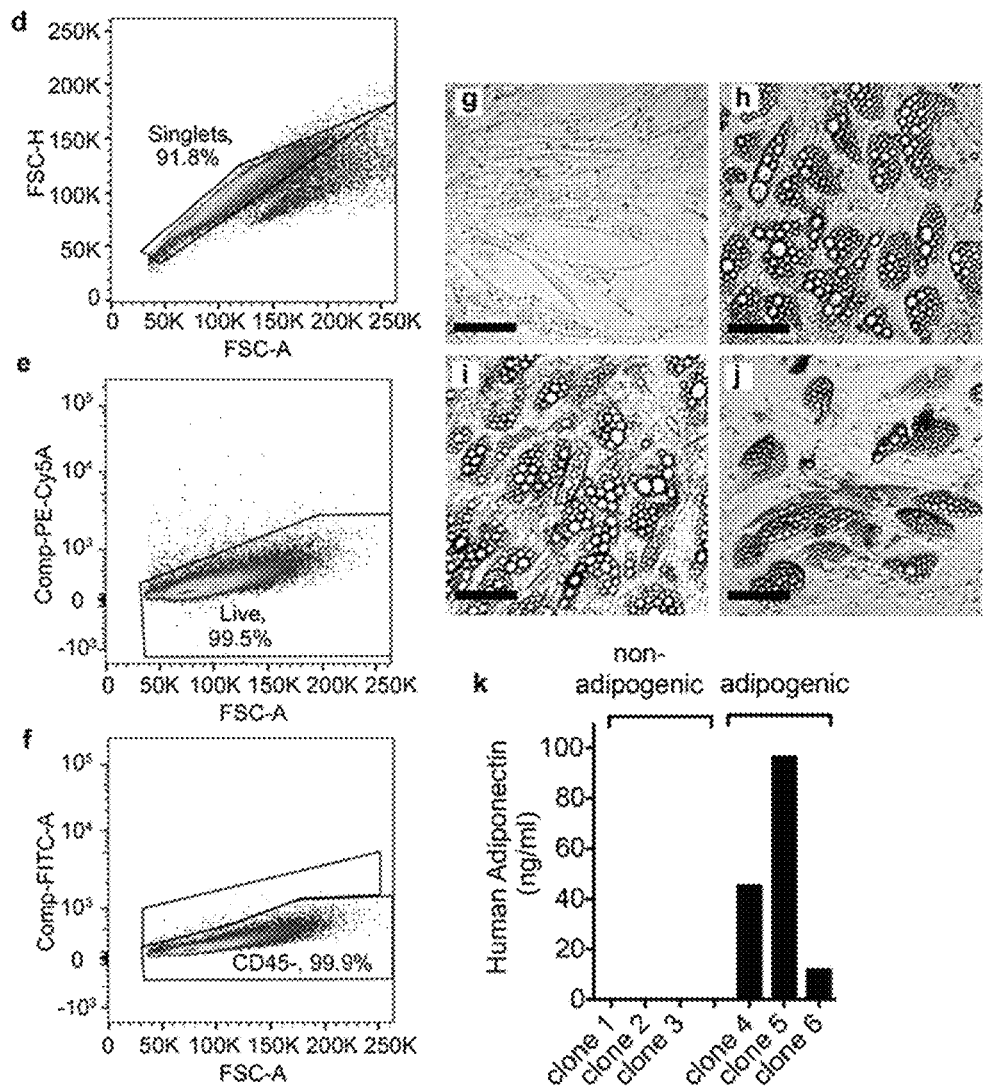
FIGURES 2D-K

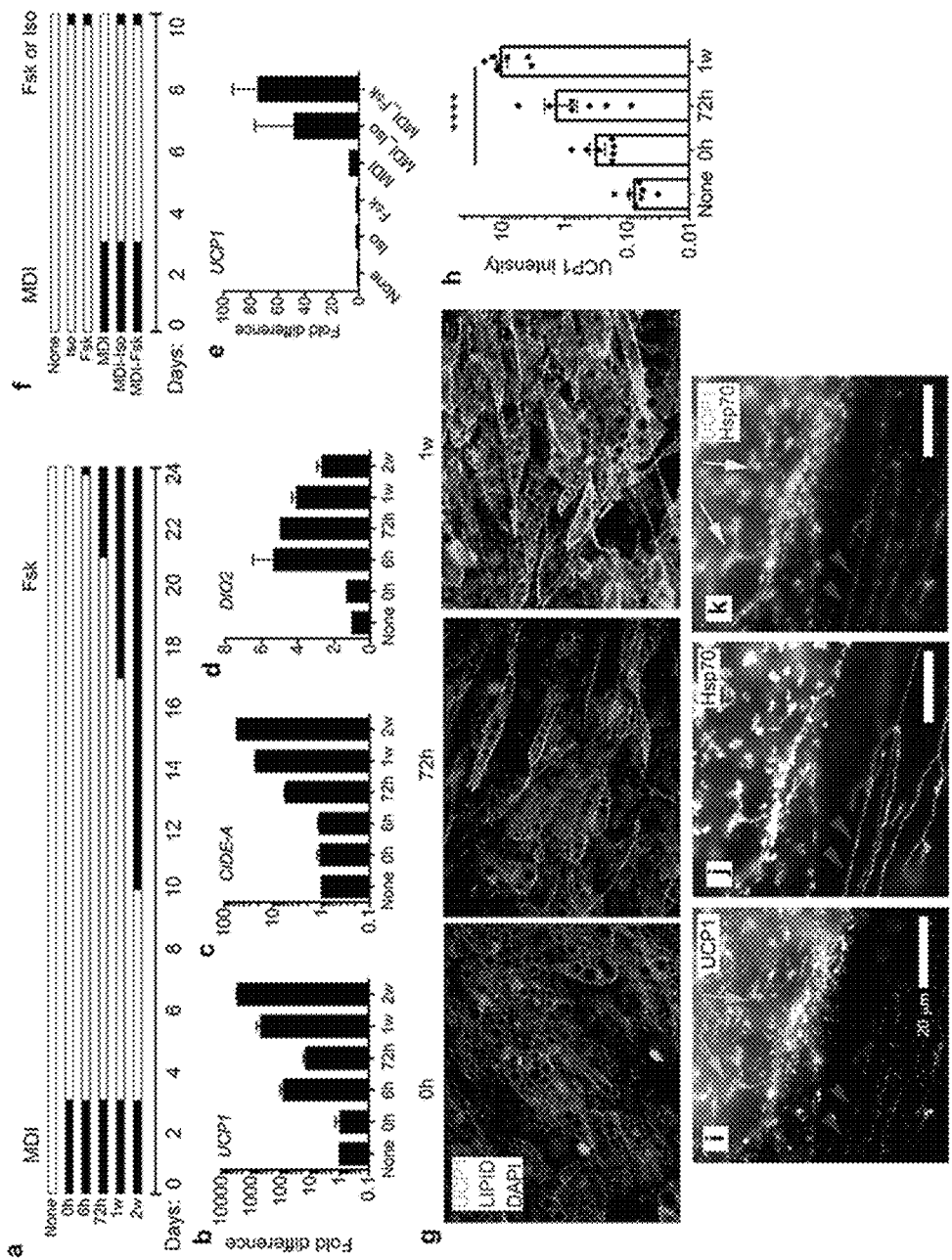
FIGURES 3A-K

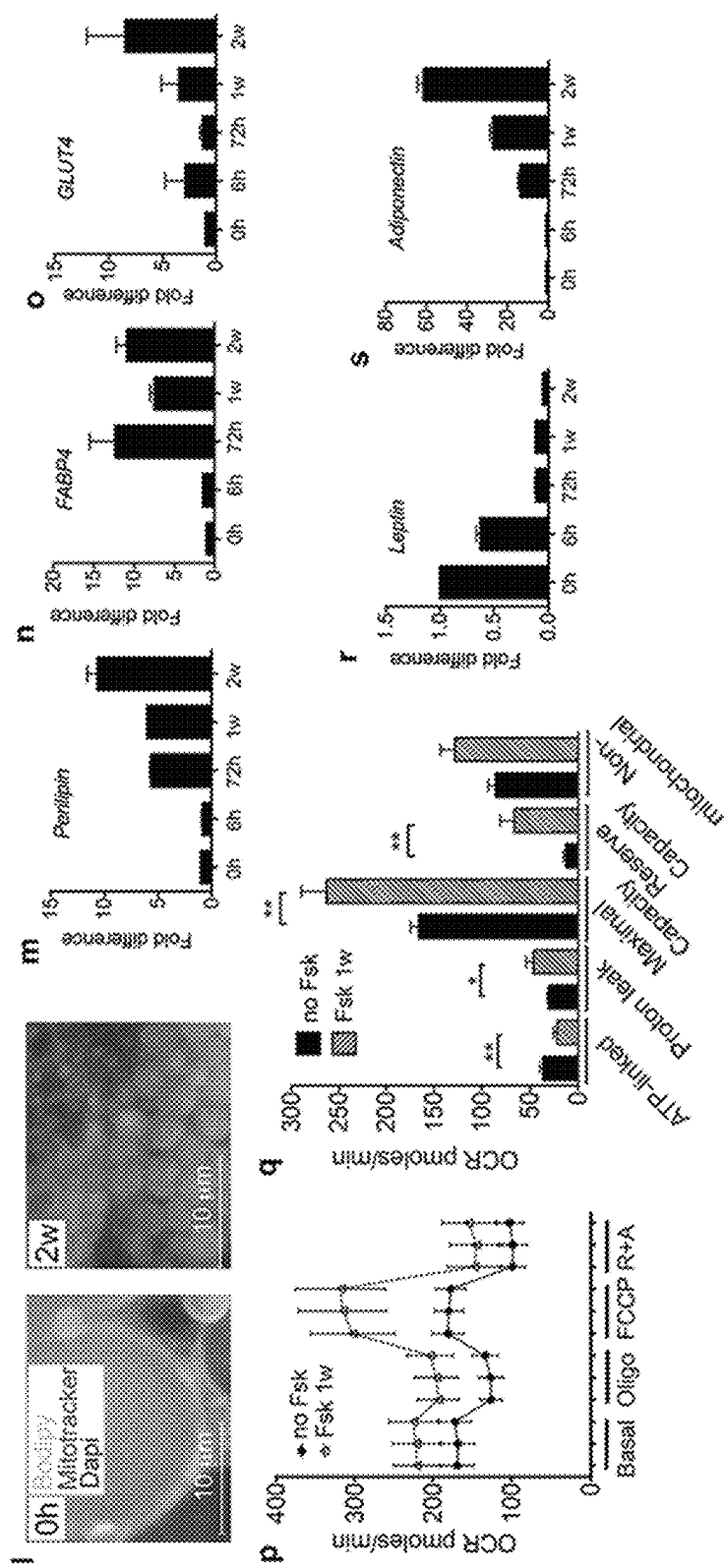
FIGURES 3L-S

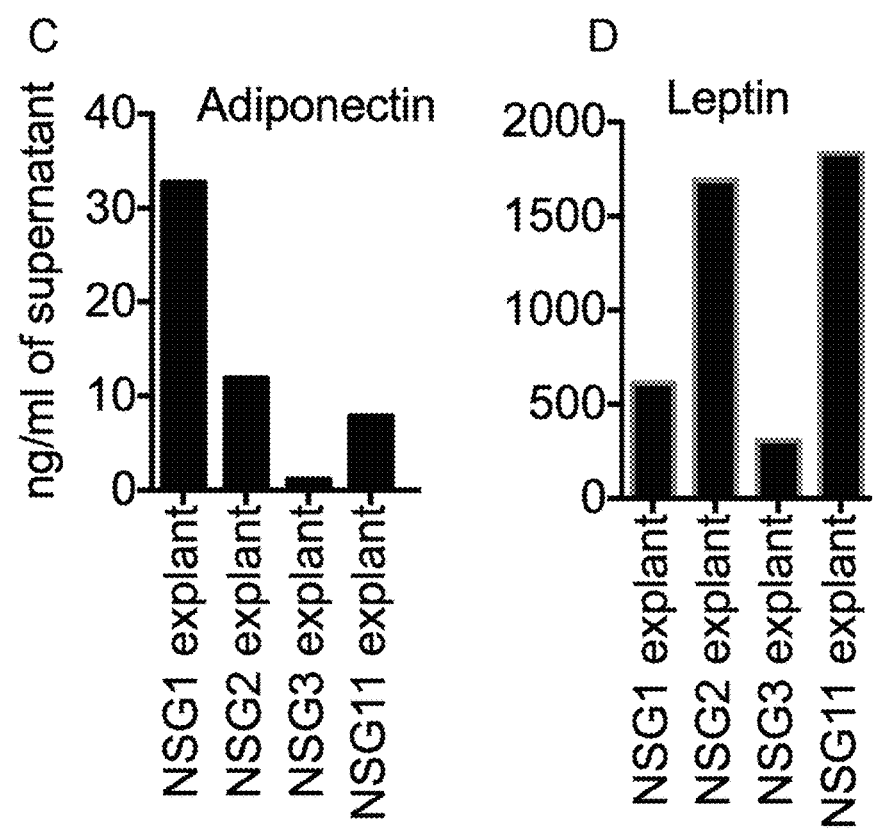
FIGURES 4A-D

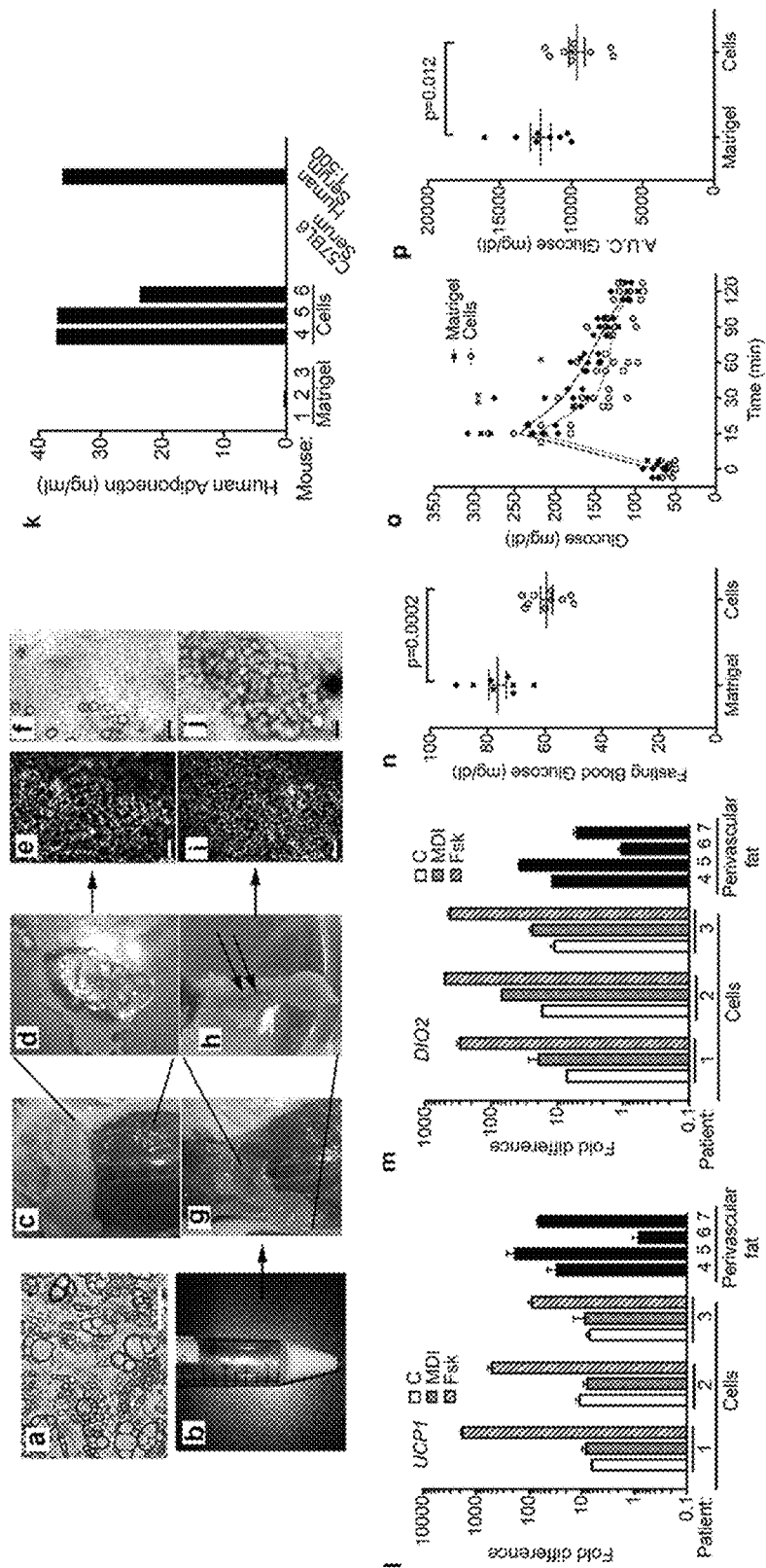
FIGURES 5A-P

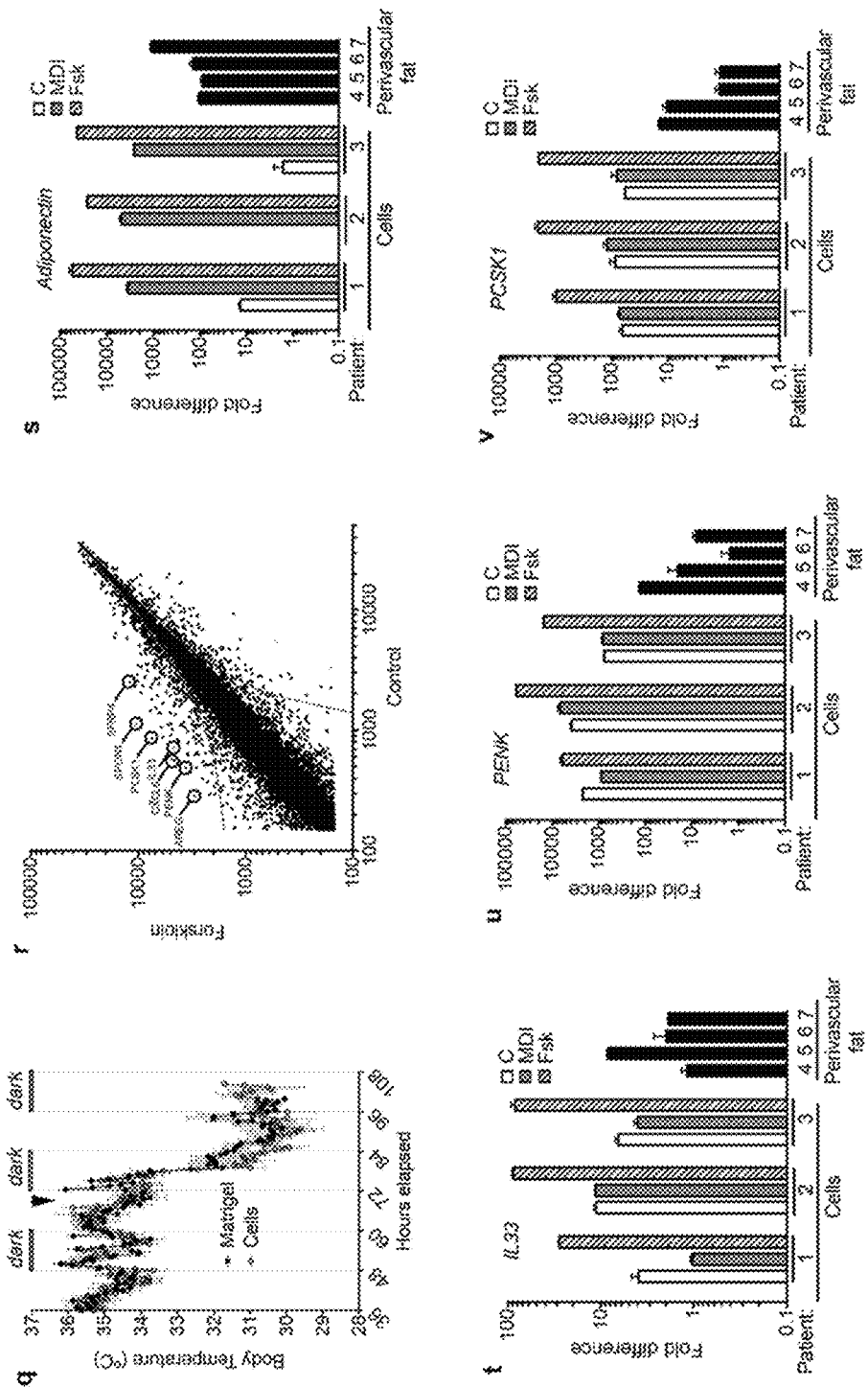
FIGURES 5Q-V

HUMAN ADIPOSE TISSUE WHITE AND 'BROWN-ON-WHITE' PROGENITORS FOR RECONSTRUCTIVE AND METABOLIC THERAPIES

CLAIM OF PRIORITY

This application claims the benefit of U.S. Provisional Patent Application No. 61/954,289, filed on Mar. 17, 2014. The entire contents of the foregoing are hereby incorporated by reference.

FEDERALLY SPONSORED RESEARCH OR DEVELOPMENT

This invention was made with Government support under Grant No. DK089101 awarded by the National Institutes of Health. The Government has certain rights in the invention.

TECHNICAL FIELD

This invention relates to methods for preparation of human adipose capillary progenitor cells (HACAPS), which are human adipose progenitor cells capable of giving rise to either white or "Brown-on-white" (Brite) adipose cells, and enriched populations thereof, for reconstructive and metabolic therapy, and for drug discovery.

BACKGROUND

Adult stem cells are preferred source for cells to be used in cell therapy methods for regenerating and repairing tissues, as they are not plagued with the problems of induced pluripotent stem cells or embryonic stem cells. Furthermore, when autologous stem cells can be used, transplant rejection and graft-versus-host disease can be avoided without the use of toxic immunosuppressive therapy. Adipose stem cells are particularly desirable given the ease of harvesting with minimally invasive procedures and the high percentage of stem cells. Human adipose tissue is a source of adult stem cells that have been shown to have differentiation capacities, being capable of generating myogenic, osteogenic and endothelial lineages (see, e.g., Baer and Geiger, Stem Cells Int. 2012; 2012:812693). Homogeneous populations of cells are desirable for use in clinical methods, but previous methods (which typically involve a culturing step) produce heterogeneous mixtures of cells with no specific prospective molecular identity.

Adipose tissue is comprised of the parenchymal cells (adipocytes) and their stomal vascular support (extracellular matrix, vasculature). Adipocytes can be classified into "white" "brown" or "brite/beige" depending on their functional role. White adipocytes primarily store excess energy in the form of triglycerides, stored in a single large droplet within their cytoplasm. Brown adipocytes primarily burn fat for the purpose of providing heat to protect organs from cold exposure. "Brite" (Brown-in-white) or "beige" adipocytes, are similar to white adipocytes in that they can store fat in droplets within the cytoplasm, but resemble brown adipocytes in that they can burn fat. Brown fat is present in hibernating animals and human infants, but is absent in human adults. However, brite/beige cells remain and can be found in the supraclavicular region, and interspersed within white adipocytes. Mice also have beige/brite adipocytes interspersed within their white adipose tissue depots. Beige/brite adipocytes are highly metabolic, and their presence is correlated with lean, insulin sensitive phenotypes. This has suggested that strategies to increase brite/beige cells would be useful for the treatment of obesity-associated diseases.

There is much interest in identifying both white and beige/brite cell progenitors in order to expand them and using them for therapeutic purposes. Uses for white adipocytes include grafting for plastic and reconstructive surgery. Uses for brite/beige adipocytes include grafting to increase metabolic rate and prevent obesity and complications. Isolation of brite/beige progenitors will also allow the development of assays to screen for drugs that will enhance their proliferation and differentiation. Approaches to identify white adipocyte progenitors have included isolation by collagenase digestion of all cells comprising the stromal vascular fraction, and selection of cells through plating on plastic. This produces a heterogeneous population of cells, which differentiate variably and poorly. Further enrichment of progenitors using fluorescence-activated cell sorting has also been attempted, but results in very low cell yields and remaining heterogeneity. Brite/beige progenitors have never been identified by this procedure. Thus, a better method to expand and identify human adipocyte progenitors is necessary.

SUMMARY

The present invention is based, at least in part, on the development of methods for preparation and expansion of Human Adipose Capillary Progenitor Cells (HACAPS), which are human progenitor cells capable of giving rise to either white or "Brown-on-white" (Brite) adipose cells, and enriched populations thereof, for reconstructive and metabolic therapy, and for drug discovery. The use of these progenitors for the discovery of small molecules and biologicals capable of selectively facilitating brite cell proliferation and/or differentiation and/or thermogenic induction is also described herein.

Thus in a first aspect the invention features methods for making an isolated, enriched population of Human Adipose Capillary Progenitor Cells (HACAPS). The methods include providing primary adipose cells or tissue from a subject, e.g., a mammal, and (i) culturing the primary cells or tissue in the presence of pro-angiogenic factors, e.g., human recombinant FGF-2, sufficient to induce the growth of a population of cells comprising capillary cells, and (ii) isolating single cells from the ensuing population of cells (comprising capillary and other cells) to form a population of cells enriched for HACAPS. In some embodiments, only proliferating (e.g., non-terminally differentiated) cells are isolated.

Pro-angiogenic factors include growth factors and components that support the growth of cells that compose blood vessels, e.g., proprietary media EGM2-MV (Lonza) or a formulation comprising Media 199 supplemented with glucose (10 mM), ascorbic acid (500 mM), hydrocortisone (1 uM) and human recombinant FGF-2 (0.1 nM). In some embodiments, the pro-angiogenic factors comprise FGF-2, and one or more of VEGF, IGF1 and EGF; for example, FGF-2 and VEGF; FGF-2 and IGF1, or FGF-2 and hEGF; or FGF-2, VEGF, and IGF; FGF-2, VEGF, and EGF; FGF-2, IGF1, and EGF; or all of FGF-2, VEGF, IGF1, and EGF are used. In some embodiments, e.g., wherein the cells used are human cells, human pro-angiogenic factors are also used.

Capillary cells are cells that compose capillary blood vessels, such as endothelial cells and pericytes, and can be identified by the formation of branched structures, tight junctions, and/or optionally by the (detection of) expression of markers such as VE-cadherin, Von Willebrand factor, and smooth muscle actin, and PDGFR2.

In some embodiments, isolating single cells from the capillary cells comprises subjecting the capillary cells to protease digestion, e.g., using dispase or other proteases that are capable of degrading fibronectin, such as Granzyme-B or MMP-9, to isolate the HACAPS. In some embodiments, the HACAPS express CD73, and the methods include a step of enriching the population for, or isolating, CD73+ cells.

In some embodiments, the methods include maintaining the HACAPS in culture for a time and under conditions sufficient for the cells to proliferate.

In some embodiments, the methods include maintaining the HACAPS in culture for a time and under conditions sufficient for the cells to differentiate into brite fat cells. In some embodiments, the HACAPS are cultured in the presence of adenylate cyclase activators such as forskolin (e.g., 1 uM) or adrenergic agonists such as isoproterenol (e.g., 10 uM), epinephrine (e.g., 10 uM), norepinephrine (e.g., 10 uM), terbutaline (e.g., 10 uM) or dobutamine (e.g., 10 uM) or thyroid hormome (T3, e.g., 10 uM), e.g., for 1 week.

Also provided herein are isolated, enriched populations of brite adipose cells made by a method described herein, and isolated, enriched population of brown adipose cells made by a method described herein.

Also provided herein are isolated, enriched populations of cells obtained from human adipose tissue capillary networks (HACAPS). In some embodiments, the cells are not transformed spontaneously or with viruses. In some embodiments, the cells are from a human.

In another aspect, the invention provides methods for treating a subject who is obese (e.g., who has a BMI of 30 or higher), or has metabolic syndrome or type 2 diabetes. The methods include administering to the subject an isolated, enriched population of HACAPS as described herein; an isolated, enriched population of brite adipose progenitor cells as described herein; and/or or the isolated, enriched population of brown adipose cells as described herein. In some embodiments, the primary adipose cells or tissue are autologous to the subject.

In a further aspect, the invention provides methods for treating a subject who is in need of adipose tissue reconstruction or regeneration. The methods include administering to the subject an isolated, enriched population of HACAPS, wherein the cells are administered to the site at which adipose tissue reconstruction or regeneration is desired.

In some embodiments, the methods include administering a population of white adipocytes as described herein. In some embodiments, the subject is in need of facial or breast reconstruction.

In some embodiments, the subject is a mammal, e.g., a human.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-D: Proliferation of adipogenic precursors requires angiogenesis. a) Time course of growth and differentiation from human explants cultured in Matrigel and the proprietary medium EGM2-MV for the times indicated. Explants were exposed to adipogenic cocktail (MDI) for the three-day interval between days 12 and 15. Arrowheads point to elongated cells forming a sprout, and arrows point to one of these accumulating lipid droplets, rounding up and detaching from the linear networks. b) RT-PCR for the human genes indicated above each graph, using RNA isolated from the growth area of explants cultured in EGM2-MV for 11 days, and then cultured for an additional 7 days in the absence (−) or presence (+) of adipogenic induction cocktail (MDI). The values indicated are the means and range of two technical duplicates, from pools of 3 explants per condition. c) Explant growth in media composed of DMEM+10% FBS in the absence (top panels) or presence (middle panels) of angiogenic growth factors (GF: VEGF, hFGF-B, hEGF, $R^3$-IGF-1), or of EGM2-MV (bottom panels) and imaged at the time point indicated above. Higher magnification of indicated areas display branched capillary structures comprising explant growth, and their accumulation of lipid droplets (arrows) in response to differentiation. d) Quantification of area growth from explants grown for 11 days under the conditions indicated. Bars represent means and SEM from 6 explants per condition using tissue from two different individuals.

FIGS. 2A-K: Clonal analysis of HACAPS. a) HACAPS were plated on tissue culture plates, grown to confluence and exposed to MDI. Images are taken from the same region, showing formation of lipid droplets of increasing size (arrows) at the indicated days following MDI treatment. Bars=50 μm; b,c) RT-PCR analysis of cDNA from HACAPS from two different individuals, exposed to vehicle or MDI (− or + MDI, respectively) for three days after confluence, and RNA extracted after 18 days. Plotted are the means and range of two technical replicates in each case; d-f) Single, live cells HACAPS used for clonal analysis were CD45−, as expected from a non-hematopoietic lineage; g-j) Single live cells give rise to non-adipogenic (g) or adipogenic (h j) clones identified by lipid droplet content. Bars=50 μm. k. Levels of adiponectin detected in culture medium from non-adipogenic (1-3) and adipogenic (4-6) clones similar to those illustrated in g-j.

FIGS. 3A-S: Induction of brite/beige phenotype in HACAPS. a-d) Analysis of UCP1 (b), CIDE-A (c) and deiodinase-2 (d) mRNA expression in differentiated HACAPS exposed to forskolin (Fsk) for 6 hours to 2 weeks as indicated in the scheme above the plotted data (a); e,f) UCP1 mRNA expression (e) in cells exposed to isoproterenol or forskolin as indicated in the scheme above the plotted data (f). Plotted are the means and range of 2 technical replicates. Similar results were obtained with cells from at least 3 different individuals; g) Immunofluorescence staining for UCP1 (green) in differentiated cells (lipid droplets pseudocolored red, nuclei blue) exposed to forskolin for the times indicated above each panel, as described in the scheme in (a); h) Means and SEM of staining intensity for UCP1 in 7 images derived from 2 independent coverslips; statistical significance was assessed using 1-way ANOVA, with Dunnett's correction for multiple comparisons: ****$p<0.0001$.

Figure 1A:
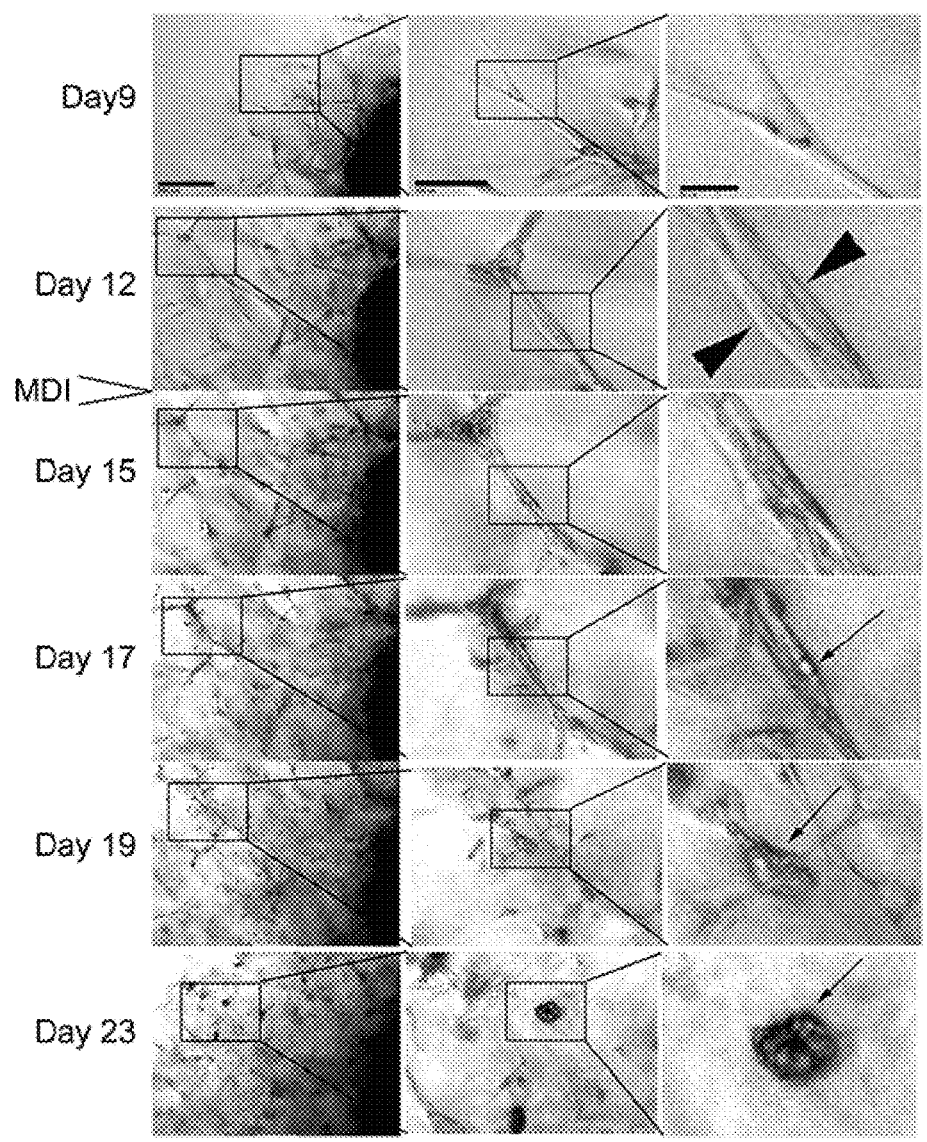

This experiment has been repeated with cells from at least 3 individuals, with similar results; i-k) Immunofluorescence staining for UCP1 (i) and mitochondrial Hsp70 (j) in cells exposed to forskolin for 1 week. Arrowheads indicate linear mitochondrial structures in cell devoid of UCP1, and arrows point to rounded mitochondrial structures containing both UCP1 and Hsp70 as evidenced by the yellow color in the image overlap (k); l) Fragmentation of lipid droplets in cells exposed to forskolin for 2 weeks (right panel), as compared to cells exposed to vehicle (left panel); m-o) Analysis of perilipn (m), FABP4 (n) and GLUT4 (o) expression in cells exposed to forskolin as indicated in the scheme above (a); p) Oxygen consumption by adipocytes exposed to vehicle or forskolin for 1 week as in the scheme above (a). The addition of reagents to determine mitochondrial state is shown in the x-axis. Plotted are the means and SEM of four experiments performed in triplicate; q) Summary data for oxygen consumption parameters. Statistical analysis was performed using two-tailed unpaired Student t-tests: **=$p<0.005$; *=$p<0.05$; r,s) Analysis of leptin (r) and adiponectin (s) expression in cells exposed to forskolin as indicated in the scheme above (a).

FIGS. 4A-D: A: site of subcutaneous injection of differentiated HACAPS in a immunocompromised NSG mouse, sacrificed at 4 weeks after injection. B: magnification of injection site at which accumulation of adipose tissue was observed. Fragments of adipose tissue collected from the injection site were incubated for 48 h, and the media then assessed for presence of human adiponectin (C) or leptin (D). No signal was detected in media collected from mouse adipocyte cultures, verifying the species-specificity of the assays.

FIGS. 5A-V: Metabolic effects and characteristics of brite/beige adipocytes derived from HACAPS. a) Phase image of cells immediately before dissociation into single sell suspension; b) Suspension of cells immediately before mixing with Matrigel and injection into each mouse; c) Dorsal area of mouse injected with Matrigel alone, revealing remnants after 4 weeks; d-f) Collected remnants of Matrigel, visualized by fluorescence (e) and phase (f) microscopy after staining with Hoechst, revealing numerous infiltrating cells, some containing lipid droplets; g) Dorsal area of mouse injected with cell/Matrigel mixture after 4 weeks, revealing well formed adipose tissue structure; h-j) excised fat structure, displaying vascularization (arrows), and further analyzed by fluorescence (i) and phase (j) microscopy after staining with Hoechst, revealing numerous cells containing lipid droplets; k) Content of human adiponectin in sera from mice receiving Matrigel alone or Matrigel/cell mixtures after 4 weeks. Serum from a C57BL6 mouse and a 1:500 dilution of normal human serum analyzed simultaneously to verify specificity of the assay for human adiponectin; l,m) Analysis of UCP1 (l), and deiodinase-2 (m) expression in cells from three individuals without (C) or with exposure to adipogenic conditions (MDI) and forskolin (Fsk) for 7 days as indicated in the scheme in FIG. 3a, compared to carotid perivascular adipose tissue excised from 4 individuals; n) Fasting glucose levels in mice implanted with Matrigel alone or cells differentiated for 14 days and exposed to forskolin for 10 days prior to implantation; o) Glucose tolerance curves with 2 g/Kg glucose after 16 h fast; p) areas under the glucose excursion from (o). For panels (n) and (p), statistical analysis was performed using two-tailed unpaired Student-t tests, and for panel (o) using 2-way ANOVA adjusted with Sidak's multiple comparisons test; q) Temperature recordings from subcutaneous iButtons in mice implanted with Matrigel or cells. Arrow represents time at which mice were placed in the cold; r) Scatter plot of gene expression levels in differentiated cells without (control) or with forskolin treatment for 7 days, indicating genes of interest outside the 95% prediction band; s-v) RT-PCR analysis of adiponectin (s), IL-33 (t), PENK (u) and PCSK1 (v) expression in cells from three individuals without (C) or with exposure to adipogenic conditions (MDI) and forskolin (Fsk) for 7 days as indicated in the scheme in FIG. 3a, compared to perivascular adipose tissue excised from 4 individuals.

DETAILED DESCRIPTION

During embryonic development, the formation of new adipocytes and the formation of the adipose tissue microvasculature are highly interdependent. Indeed, during embryonic development, the formation of the adipose tissue vascular network precedes the emergence of adipocytes (Han et al. Development. 2011; 138(22):5027-37). Also, in adult mice, expansion of adipose tissue is accompanied by formation of angiogenic foci (Nishimura et al. Diabetes. 2007; 56(6):1517-26). In addition, in mice, adipose tissue capillary walls are a niche for adipocyte progenitors (Tang et al., Science. 2008; 322(5901):583-6; Tang et al., Cell Metabolism. 2011; 14(1):116-22). New adipocytes form from cells tightly embedded in the walls of newly formed human adipose tissue capillaries (Tran et al., Cell Metabolism. 2012; 15(2):222-9). These newly emerging adipocytes contain key adipocyte-specific markers, yet are connected to endothelial cells through tight junctions, supporting the concept that they are tightly associated with the capillary wall (Tran et al., Cell Metabolism. 2012; 15(2):222-9). Lineage-tracing studies using reporters driven by the VE-cadherin promoter clearly show that at least some adipocytes are derived from progenitors that at some point during development expressed VE-Cadherin (CD144) (Tran et al., 2012). Thus, even in adult organisms the development of the adipose tissue microvasculature and the formation of new adipocytes may be interdependent.

Numerous studies report the presence of pluripotent stem cell populations in human adipose tissue that hold great potential for clinical applications (see review by Baer and Geiger, Stem Cells Int. 2012; 2012:812693). For example, one of the therapeutic uses of adipose tissue is in reconstructive surgery, where adipose tissue is grafted for the purpose of contour filling or replacement of tissue following excision of tumors. However, this grafted tissue consists mostly of mature adipocytes, which do not proliferate and are eventually reabsorbed. In an attempt to improve adipose tissue grafting, adipose tissue has been supplemented with cells derived from the stromal vascular fraction (SVF) (Yoshimura et al., Breast J. 2010; 16(2):169-75; Yoshimura et al., Dermatol Surg. 2008; 34(9):1178-85; Yoshimura et al., Regen Med. 2009; 4(2):265-73). The positive results obtained from this procedure, including longer graft duration, are attributed to the presence of precursor stem cells within the SVF. Production of, and enrichment for, true stem cells capable of regenerating adipocytes and their vasculature would greatly enhance the effectiveness of adipose tissue use for reconstructive purposes.

In addition, adipose tissue precursors may also be critical determinants of adipose tissue expandability. In most published studies related to adipose tissue stem cells, cells were selected on the basis of their plating properties and growth in-vitro, and comprise a mixed population with no specific prospective molecular identity.

Methods of Obtaining Enriched Populations of Human Adipose Capillary Progenitor Cells (HACAPS)

As demonstrated herein (see Example 1 below), subcutaneous adipose tissue fragments cultured ex-vivo, e.g., embedded in MatriGel and incubated in the presence of angiogenic growth factors, produce capillary networks that contain adipocyte progenitors.

The methods include obtaining primary adipose cells or tissue from a subject, e.g., a mammal, e.g., a human or veterinary subject. The primary adipose cells or tissue can be obtained using methods known in the art, e.g., surgical harvesting, needle biopsy, or lipoaspiration. The tissue (2-10 g, e.g., 3-7 g, preferably about 5 g) is then cut, e.g., into 1 mm pieces, which are embedded in a protein-gel matrix; one preferred example of a matrix is MatriGel (a gelatinous protein mixture secreted by Engelbreth-Holm-Swarm (EHS) mouse sarcoma cells, marketed by Corning Life Sciences and by Trevigen, Inc., under the name Cultrex BME, that includes a complex mixture of basement membrane proteins such as laminin, type IV collagen, entactin/nitrogen and proteoheparan sulfate, and also contains growth factors; see Hughes et al., Proteomics. 2010 May; 10(9):1886-90; Benton et al., J Cell Physiol. 2009 October; 221(1):18-25; Kleinman and Martin, Semin Cancer Biol. 2005 October; 15(5):378-86; and Baatout and Cheta, Rom J Intern Med. 1996 July-December; 34(3-4):263-9), though other extracellular matrix substitutes and bioscaffolds can also be used, e.g., the PathClear® Grade Basement Membrane Extract (AMSBIO); StemXVivo™ Culture Matrix (R&D Systems); or StemAdhere™-Defined Matrix (Stemcell Technologies). The tissue is then cultured in medium formulated for endothelial cell growth, e.g., supplemented with glucose (10 mM), hydrocortisone (3 uM), ascorbic acid (1 mM), and human FGF-2 (0.1 nM). In some embodiments, the medium is supplemented with pro-angiogenic factors. In some embodiments, the pro-angiogenic factors comprise FGF-2, and one or more of VEGF, IGF1 and EGF; for example, FGF-2 and VEGF; FGF-2 and IGF1, or FGF-2 and hEGF; or FGF-2, VEGF, and IGF; FGF-2, VEGF, and EGF; FGF-2, IGF1, and EGF; or all of FGF-2, VEGF, IGF1, and EGF are used. In some embodiments, e.g., wherein the cells used are human cells, human pro-angiogenic factors are also used. In some embodiments, the medium is EGM™2-MV, a medium formulated for endothelial cell growth (Lonza Biologics).

The cultures are maintained for a time sufficient for capillary growth to occur; capillary growth is recognized by the formation of branched structures comprised of at least three connected cells. After the culture dishes exhibit a desired amount of capillary growth, e.g., the point at which capillary tip cells reach the edge of the culture dish, the obtained adipose progenitor cells (HACAPS) can be harvested, and employed for various uses, e.g., reconstructive surgery.

The present invention can include harvesting the cells after recovery from Matrigel in a single cell suspension. The protein-gel matrix is degraded by proteolysis, e.g., using dispase for Matrigel. Other proteases that degrade fibronectin, such as Granzyme-B or MMP-9 could also potentially be used. Because some cells attach to the bottom of the plate, mechanical or (preferably) enzymatic treatment (e.g., with a protease such as trypsin, thermolysin, pepsin, or collagenase; in some embodiments, trypsin/EDTA (e.g., Trypsin-Versene™ (Lonza)), TrypLE™ (Life Technologies) or Detachin Cell Detachment Solution (Genlantis)) can be used for detaching cells that remain adherent to the well, e.g., after the matrix is degraded treatment. For example, the cultures can be incubated in dispase at 37° C. for 1.5-2 hours, and then a Trypsin-Versene/EDTA mixture is used to stop the matrix (dispase) digestion and dislodge adherent cells. The cell suspension obtained is then placed in medium, e.g., EGM™-2 MV supplemented EBM-2 medium, and the cells are concentrated, e.g., by centrifugation, e.g., at 2000 rpm for 10 minutes at room temperature. At this point the cell suspension is heterogeneous, but adipocyte progenitors represent at least 50% of clonally expandable population, and express the cell surface marker CD73, which can be used to further purify the cells. The HACAPS thus obtained are then resuspended in media; these cells can be further cultured and passaged. As shown in FIG. 2, HACAPS are capable of differentiation and clonal expansion.

Another approach to obtaining adipocyte progenitors (HACAPS) is to use primary adipose cells or tissue collected from a subject (see above) that is then dissociated, e.g., by collagenase digestion or mechanical disruption, into a heterogeneous mixture of primary cells that likely includes mature adipose cells, stem cells, and other cell types present in the adipose tissues, e.g., endothelial or epithelial cells. The mixture of primary cells is then resuspended in media, e.g., EGM™-2 MV supplemented EBM-2 medium, or in Media 199 supplemented glucose (10 mM), hydrocortisone (3 uM), ascorbic acid (1 mM), and human FGF-2, (0.1 nM). After 12 hours, any non-adherent cells are removed. The cells that attach and proliferate are mixed, but are highly enriched for adipocyte progenitors.

This mixture of cells is then sorted or immunoadsorbed based on the expression of one or more cell surface markers, e.g., CD29 and/or CD73 plus CD44 and CD90, to produce enriched populations of cells, e.g., an enriched population of CD45−CD34−CD24−CD29+CD44+CD90+CD73+ cells (which are brite fat progenitor cells) and/or an enriched population of cells that are CD45-CD29+CD34+CD24+CD144− (white fat progenitor cells). Methods for sorting cells are known in the art, and include flow cytometry, e.g., fluorescence activated cell sorting (FACS), using fluorescently labeled antibodies that recognize the cell surface markers. When fluorescence detection is used, the primary antibodies can be labeled, or can be detected using labeled secondary antibodies. Suitable antibodies are known in the art and commercially available, e.g., from BD Biosciences. Other flow cytometric cell sorting methods can also be used, e.g., photoacoustic (PA), photothermal (PT), fluorescent, and Raman methods (see, e.g., Glanzha and Zharov, Methods. 2012 July; 57(3):280-96); photon flow cytometry strategies and applications; see, e.g., Tkaczyk and Tkaczyk, Cytometry A. 2011 October; 79(10):775-88; and microfluidic impedance-based flow cytometry (see Cheung et al., Cytometry A. 2010 July; 77(7):648-66). As an alternative, other methods such as magnetic cell sorting (MACS) and microfluidic cell sorting methods can also be used; see, e.g., Autebert et al., Methods. 2012 July; 57(3):297-307; Zhao et al., Molecules. 2012 May 25; 17(6):6196-236; Smith et al., Semin Reprod Med. 2011 January; 29(1):5-14; Bhagat et al., Med Biol Eng Comput. 2010 October; 48(10):999-1014; and Bernstein and Hyun, Stem Cell Res Ther. 2012 May 10; 3(3):17.

Enriched Populations of Adipose Progenitor Cells

The present invention also includes enriched populations of adipose progenitor cells, i.e., populations of cells isolated by the methods described herein wherein at least 20% of the cells are adipose progenitor cells or HACAPS, e.g., at least 50%, e.g., at least or more of the cells are adipose progenitor cells or HACAPS, e.g., cells that express the cell surface marker CD73 (CD73+ cells). In some embodiments, the enriched populations comprise primary cells, i.e., cells that have never been plated but were obtained directly from an animal, e.g., a mammal, e.g., an experimental animal or a human or veterinary subject, or cells that are being plated for the first time.

Vertebrate tissue can be obtained by standard methods such a biopsy or other surgical methods of obtaining a tissue source of the primary cell type of interest. For example, panniculectomy surgery, liposuction, bariatric surgery, or needle biopsy can be is used to obtain adipose tissue as a source of primary adipose progenitor cells. The tissue is then dissociated into cells, using known methods, such as mechanical disruption, trituration, or enzymatic digestion or explanting. If enzymatic digestion is used, enzymes such as collagenase, hyaluronidase, dispase, pronase, trypsin, elastase and chymotrypsin can be used. Any method can be used so long as the cells obtained are viable. A mixture of primary cells is typically obtained from the tissue.

Differentiating Adipose Progenitor Cells

In some embodiments, after the adipose progenitor cells or HACAPS are obtained and optionally enriched, e.g., by a method described herein, the cells are plated and then maintained in culture to proliferate or differentiate.

In some embodiments, the adipose progenitor cells or HACAPS can be genetically engineered to stably or transiently express one or more exogenous genes, or to lack or underexpress one or more endogenous genes using methods known in the art. For example, the cells can be transfected with an exogenous nucleic acid sequence that includes a nucleic acid sequence encoding a selected protein or peptide, and produce the encoded product stably and reproducibly in vitro and in vivo, over extended periods of time. A heterologous amino acid can also be a regulatory sequence, e.g., a promoter, which causes expression, e.g., inducible expression or upregulation, of an endogenous sequence. An exogenous nucleic acid sequence can be introduced into a primary or secondary cell by homologous recombination as described, for example, in U.S. Pat. No. 5,641,670, the contents of which are incorporated herein by reference. The transfected primary or secondary cells may also include DNA encoding a selectable marker which confers a selectable phenotype upon them, facilitating their identification and isolation.

In some embodiments, the adipose progenitor cells or HACAPS are maintained in culture, differentiated into adipocytes (e.g., by incubation in the presence of MDI), and then used directly in reconstructive surgery.

In some embodiments, the initial primary adipose cells are obtained by needle biopsy from an individual scheduled to undergo plastic and/or reconstructive surgery. The adipose progenitor cells or HACAPS are generated and then used directly or to enrich the individual's own adipose tissue which is harvested and used during the surgery.

In some embodiments, the adipose progenitor cells or HACAPS are used to seed scaffolds, which can be used directly, or after the seeded adipose progenitor cells within the scaffold have been induced to differentiated in-vitro into adipocytes, e.g., by incubation in the presence of MDI (synthetic glucocorticoid dexamethasone, the cAMP elevating agent 1-methyl-3-isobutyl xanthine (MIX), and pharmacological doses of insulin; see Hwang et al., Annu Rev Cell Dev Biol 13: 231-259).

The adipose progenitor cells or HACAPS can be differentiated into adipocytes and cultured, e.g., in the presence of forskolin or adrenergic agonists such as isoproterenol, epinephrine, norepinephrine, terbutaline or dobutamine, or the thyroid hormone tri-iodo-thyronine (T3), to induce a brite adipocyte phenotype.

For example, to differentiate into brite fat cells, the HACAPS can be cultured, e.g., in proprietary media EGM2-MV (Lonza) or a formulation consisting of Media 199 supplemented with glucose (e.g., 10 mM), ascorbic acid (e.g., 500 mM), hydrocortisone (e.g., 1 uM) and human recombinant FGF-2 (e.g., 0.1 nM), until confluence is reached, and then exposed to adipogenic cocktail, e.g., comprising DMEM containing 10% FBS, methylisobutyl xanthine (e.g., 500 uM), dexamethasone (e.g., 100 nM) and insulin (e.g., 1 uM) for 3 days. The cells are then cultured for an additional time, e.g., 5-10 days, e.g., 7 days in media, e.g., in DMEM containing 10% FBS, and then in the same medium supplemented with adenylate cyclase activators such as forskolin (e.g., 1 uM) or adrenergic agonists such as isoproterenol (e.g., 10 uM), epinephrine (e.g., 10 uM), norepinephrine (e.g., 10 uM), terbutaline (e.g., 10 uM) or dobutamine (e.g., 10 uM) or to thyroid hormone (T3, e.g., 10 uM) for 1 week to induce differentiation of the HACAPS into brite cells. These methods are exemplary, and other methods can also be used.

These differentiated brite or brite-like cells can then be used, e.g., for transplantation, e.g., for the purpose of enhancing resting energy metabolism.

METHODS OF USE

The populations of cells described herein can be used to treat subjects. For example, populations of brite progenitor cells can be used to treat subjects who are obese, or who have metabolic syndrome or type 2 diabetes. The populations of cells described herein can be used to treat subjects; see, e.g., Gir et al., Plast Reconstr Surg. 2012 June; 129(6): 1277-90; Sterodimas et al., J Plast Reconstr Aesthet Surg. 2010 November; 63(11):1886-92; Mizuno et al., Stem Cells. 2012 May; 30(5):804-10; Marra and Rubin, Birth Defects Res C Embryo Today. 2012 March; 96(1):95-7; Brown et al., Plast Reconstr Surg. 2010 December; 126(6):1936-46. For example, populations of brown fat progenitor cells (CD45−CD29+CD44+CD90+CD73+CD105−CD34−CD24−CD144−) can be used to treat subjects who are obese (e.g., who have a BMI of 30), or who have metabolic syndrome or type 2 diabetes, e.g., as described in Tran and Kahn, Nature Reviews Endocrinology 6, 195-213 (2010).

As another example, adipose progenitor cells, e.g., white fat progenitor cells, can be used to treat subjects who are in need of adipose tissue regeneration, e.g., in reconstructive or plastic surgery, where adipose tissue is grafted into a subject for the purpose of contour filling or replacement of tissue following excision of tumors or other tissues, or after trauma. In some embodiments, the subject is undergoing facial or breast reconstruction.

For clinical use, primary cells are preferably autologous, i.e., obtained from the same individual to whom the populations of cells are to be administered.

Methods known in the art can be used to administer the cells, e.g., as described in Tran and Kahn, Nature Reviews Endocrinology 6, 195-213 (April 2010); Attached Yoshimura et al (Yoshimura et al., Breast J. 2010; 16(2): 169-75; Yoshimura et al., Dermatol Surg. 2008; 34(9):1178-85; Yoshimura et al., Regen Med. 2009; 4(2):265-73). For example, the cells can be administered by subcutaneous injection, site-specific transplantation, injection into a specific tissue, or intravenous injection, e.g., wherein the ASCs home to the injured tissue (see, e.g., Lee et al., J. Orthop. Res. 27, 295-302 (2009); Kim et al., Int. J. Cardiol. 146(3): 371-8 (2011)).

In some embodiments, the methods include transplanting the HACAPS alone, or transplanting fully differentiated brown or white adipocytes together with the HACAPS described herein. For example, white adipocytes and white adipocyte precursor cells can be transplanted together into a subject to effect adipose tissue regeneration or to treat a lipodystrophy or metabolic disorder; brown adipocytes and brown adipocyte precursor cells can be transplanted together into a subject to treat obesity, metabolic syndrome, or Type 2 diabetes. See, e.g., Tran and Kahn, Nature Reviews Endocrinology 6, 195-213 (2010).

In another application cells are used in high throughput screens to discover small molecules or biological agents that enhance growth, differentiation and/or thermogenic capacity of these cells, e.g., for use in vitro or in vivo. The HACAPS obtained by a methods described herein are used in high throughput screens to discover small molecules capable of facilitating growth and differentiation of human "brite" adipocytes. Small molecules or biologicals that specifically enhanced growth of HACAPS and not fibroblasts, or small molecules or biological that enhanced the differentiation and/or thermogenic capacity of HACAPS could be discovered. These drugs could have therapeutic potential for inducing thermogenesis and increasing basal metabolic rates for the purpose of combating obesity and associated metabolic complications. Thus, the HACAPS can be used for high throughput screening applications.

In another application, HACAPs can be used to identify secreted factors that can enhance metabolism or cell grafting. In this application HACAPS obtained by the methods described above are cultured and secreted factors (proteins, lipids) detected by mass spectrometry. These may include enkephalins, which are products of the convertase PCSK1, acting on the proenkephalin PENK, which are found in HACAPS differentiated into brown adipocytes.

Methods of Screening

Included herein are methods for screening test compounds, e.g., polypeptides, polynucleotides, inorganic or organic large or small molecule test compounds, to identify agents useful in the treatment of obesity. The methods include contacting the HACAPS, brite, white, or brown adipocytes obtained by a method described herein with a test compound, and identifying those compounds that have a desired effect on the cells.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample comprising HACAPS, brite, white, or brown adipocytes obtained by a method described herein, and one or more effects of the test compound is evaluated. In HACAPS, for example, an assay can be performed to determine the ability of the test compound to induce differentiation to a brown/brite phenotype (e.g., by detecting expression of Uncoupling Protein 1 (UCP-1), Cell Death-Inducing DFFA-Like Effector A (CIDEA) and/or deiodinase), or to a white phenotype (e.g., by detecting expression of Lipoprotein Lipase (LPL), leptin, glucose transporter-4 (GLUT-4) and/or CCAAT/enhancer binding protein (C/EBP), alpha (C/EBP-a)). In white adipocytes, the ability to shrink the cells, or cause transdifferentiation to a brown or brite phenotype can be tested (e.g., by detecting expression of UCP-1, CIDEA and/or deiodinase). In brown or brite cells, the ability to cause the cells to proliferate, or to have increase metabolic rate (e.g., by assaying thermogenic oxygen consumption), can be tested.

Methods for evaluating each of these effects are known in the art. For example, ability to modulate expression of a protein can be evaluated at the gene or protein level, e.g., using quantitative PCR or immunoassay methods. In some embodiments, high throughput methods, e.g., protein or gene chips as are known in the art (see, e.g., Ch. 12, Genomics, in Griffiths et al., Eds. *Modern genetic Analysis*, 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect an effect on expression of UCP-1, CIDEA and/or deiodinase.

A test compound that has been screened by a method described herein and determined to have a desired effect can be considered a candidate compound or a "hit". Test compounds identified as candidate compounds can be further screened by administration to an animal model of a disorder, e.g., obesity (e.g., an obese animal, e.g., diet-induced obesity and/or genetically induced obesity) or an animal with wasting (e.g., wasting associated with chronic disease or genetics). The animal can be monitored for a change in the disorder, e.g., for an improvement in a parameter of the disorder, e.g., a parameter related to clinical outcome. In some embodiments, the disease is obesity and the parameter is weight, and an improvement would be weight loss; alternatively the parameter can be risk of a metabolic disorder (such as type 2 diabetes), systemic inflammation, or insulin resistance; a decrease in any of these would also be an improvement in the disorder. In some embodiments, the disease is wasting or insufficient fat (e.g., wasting associated with exposure to toxins, chronic disease or genetics), and an improvement would be an increase in white fat. In some embodiments the test compound is screened for the ability to promote engraftment of a cell transplant, e.g., a transplant of HACAPS, or of white or brite/brown cells, as described herein.

A candidate compound that has been screened, e.g., in an in vivo model of a disorder, e.g., obesity (e.g., an obese animal, e.g., diet-induced obesity and/or genetically induced obesity) or an animal with wasting (e.g., wasting associated with exposure to toxins, chronic disease or genetics), and determined to have a desirable effect on the disorder, e.g., on one or more symptoms of the disorder, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified in a cell or animal screen as described herein can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating disorders associated with obesity or wasting. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

EXAMPLES

The invention is further described in the following examples, which do not limit the scope of the invention described in the claims.

Example 1

Figure 1B:
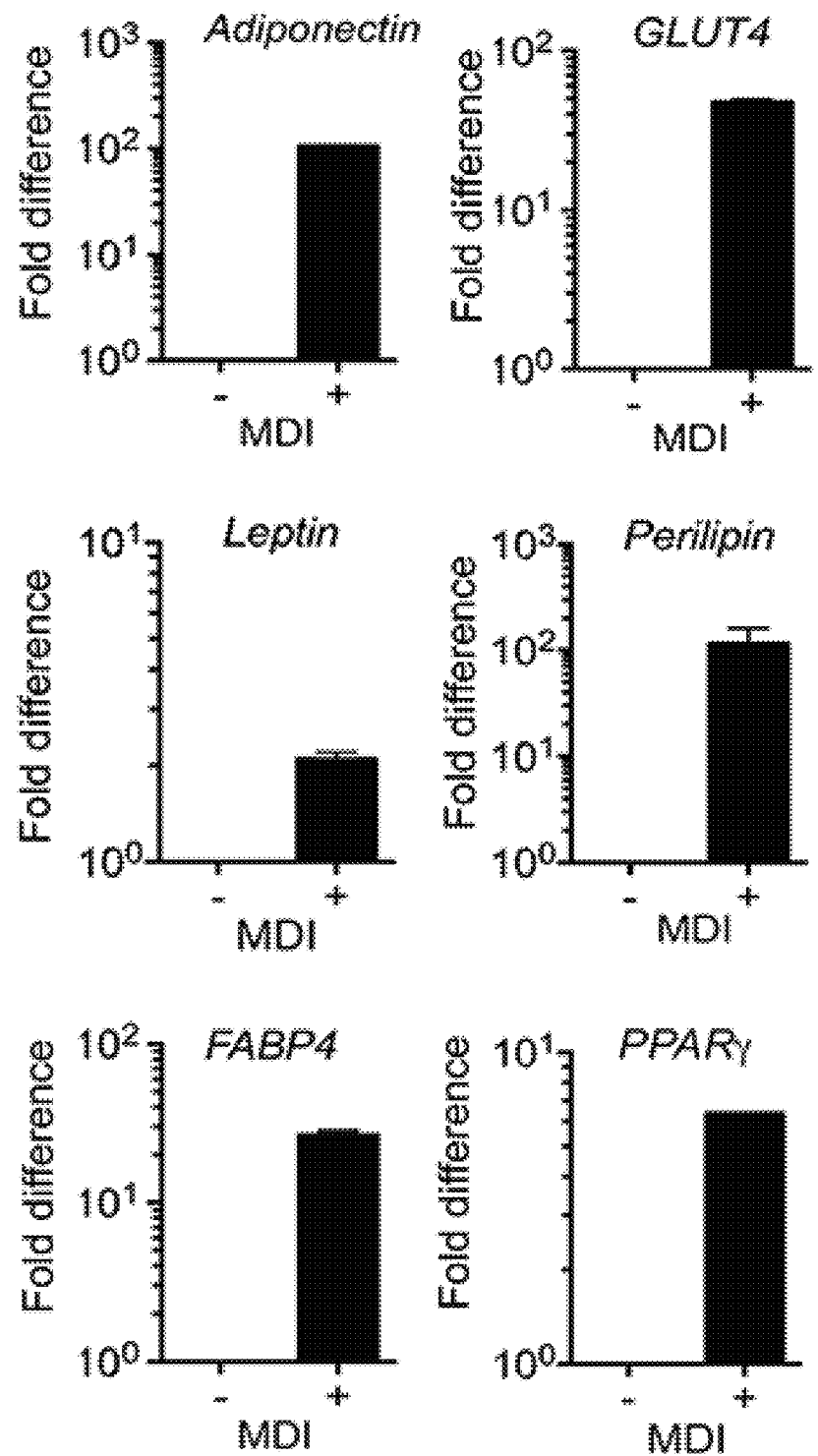

As described herein, adipocytes are formed in close proximity to vasculature generated in-vitro from human adipose tissue depots. Several previous findings in mouse models (see, e.g., Tang et al. Science 322, 583-586 (2008); Gupta et al., Cell metabolism 15, 230-239 (2012); and Tang et al., Cell Metab 14, 116-122 (2011)) suggested that the niche (i.e. the specialized cellular environment required for survival and proliferation) for mouse adipocyte progenitor cells might be the microvasculature of adipose tissue. This possibility may also apply to human adipocyte progenitor cells, but this was yet unproven. A corollary to this concept is that in order for adipocyte progenitors to proliferate, the entire capillary network must proliferate. This possibility was tested by placing small fragments of human adipose tissue under pro-angiogenic conditions ex-vivo. As follows: human adipose tissue obtained from needle biopsies, bariatric surgery, or panniculectomy procedures is cut into ~1 g fragments, from which large vessels and obvious connective tissue are removed using iris scissors. After harvesting, adipose tissue is placed into 50 ml conical tubes containing 25 ml of EGM-2 MV supplemented EBM-2 medium. The tissue is transferred from 50 ml conical tube into a culture plate, and using forceps and scalpel, cut into strips (FIG. 1). The strips into small slices not greater than 1 $mm^3$. Approximately 75-80 slices per tissue sample can be cut. Using the forceps, 1 piece of adipose tissue is placed into culture dishes containing a thin film of ice-cold Matrigel. Matrigel is kept on ice as the tissue is placed. After embedding, plate is transferred to incubator at 37° C. in 5% $CO_2$ for 30 minutes. Culture media is then added to the plate and cultured continued for 11 days. This led to growth of capillary branches ex-vivo, as well as cells associated with the capillaries. The growth of capillaries was absolutely dependent on the presence of angiogenic growth factors, and enhanced under conditions perfected for angiogenic growth (EGM-2-mv media, proprietary) (FIG. 1A-C)).

It was then discovered that cells contained within this capillary outgrowth can be differentiated into adipocytes upon exposure to an adipogenic cocktail containing dexamethasone, methylisobutyl-xanthine and insulin. To determine whether adipocyte progenitors reside within capillary networks, cultures grown for 11 days were exposed to a classical adipogenic cocktail consisting of DMEM containing methylisobutyl xanthine (500 uM), dexamethasone (100 nM) and insulin (1 uM). After 3 days, the cocktail was removed and cells fed with DMEM. After 7 days numerous lipid droplets were seen to accumulate in cells that were associated with the capillary networks and RT-PCR analysis confirmed that cells displaying lipid droplets express canonical adipocyte-specific genes adiponectin, GLUT4, and leptin, and markedly induce perilipin and FABP4 (FIGS. 1B-C). These results demonstrated that proliferation of adipocyte progenitors from adult human adipose tissue is dependent on angiogenic growth.

Example 2

As described in this example, individual cells can be isolated from in-vitro grown capillary branches. Exposure of the explant to a cocktail of dispase (see below) results in the recovery of a single cell suspension that can be subsequently plated in plastic culture dishes and subjected to differentiation (FIG. 2A). The procedure was as follows: the medium was carefully removed by aspirating it from the wells, and the cells were rinsed twice with sterile Dulbecco's Phosphate-Buffered Saline (DPBS). Dispase solution (1 U/ml) was added to cover the Matrigel and explant growth. The culture was then incubated at 37° C. for 1.5-2 hours. Forceps were used to remove remaining the explant from wells. Sufficient DPBS was added to enable mixing of cell suspension by pippeting up and down. The cell suspension was transferred from all wells to a 15 ml conical tube, which was the filled with EGM-2™ MV-supplemented EBM-2 medium to achieve a final volume of 10 ml. The tube containing the cells was centrifuged at 2000 rpm for 10 minutes at room temperature. The supernatant was aspirated and the pellet resuspended in 1 ml of fresh EGM-2 MV supplemented EBM-2 medium. These cells could be frozen for further expansion.

When the cells recovered as above were plated in standard tissue culture dishes, allowed to reach confluence and subjected to adipogenic differentiation by exposure for three days to DMEM containing 10% fetal bovine serum, methylisobutyl xanthine (500 uM), dexamethasone (100 nM) and insulin (1 uM) (MDI), the cells accumulated lipid droplets and induced the canonical markers of adipocyte identity (adiponectin, perilipin, GLUT4 and leptin) (FIGS. 2B-C). In addition, single cells could be individually cloned, and many of them maintained the capacity to undergo adipocyte differentiation (FIGS. 2G-K).

Cells obtained from stromovascular fraction of human adipose tissue compared to HACAPS were analyzed by FACS. Table 1 shows the percent of cells labeled with antibodies to the markers indicated in the lefthand column. A marked enrichment in CD73 was observed in HACAPS compared to SVF.

Thus, these methods can be used to obtain populations or clones of human adipocyte progenitor cells (HACAPS) through expanding the vasculature of adipose tissue in-vitro and then preparing single cell suspensions of HACAPS from the expanded vasculature. These cells can be used for further expansion and therapeutic application for reconstructive surgery.

TABLE 1

Enrichment of CD73 in HACAPS.

| Marker | SVF (%) | HACAPS (%) |
|---|---|---|
| CD29+ | 99.5 | 99.9 |
| CD44+ | 99.4 | 99.9 |
| CD90+ | 99.4 | 98.8 |
| CD73+ | 10.6 | 98.3 |
| CD105+ | 20.2 | 0.64 |
| CD24+ | 0.2 | 0.36 |
| CD144+ | 0.17 | 0.3 |
| CD34+ | 0.26 | 0.11 |
| CD45+ | 0.09 | 0.03 |

Example 3

Based on the finding that proliferation of HACAPS is dependent on pro-angiogenic conditions, the hypothesis was also tested that the small number of these cells present within the entire population of cells isolated by collagenase digestion from fresh adipose tissue stromovascular fraction, would preferentially proliferate if placed under pro-angiogenic growth conditions. Indeed, the number of cells capable of adipocyte differentiation increased dramatically when the plating and culture was done in pro-angiogenic medium, i.e., medium supplemented with growth factors and components capable of supporting the proliferation and differentiation of cells that compose blood vessels e.g. proprietary media EGM2-MV (Lonza). Thus, these methods can be used to enrich for HACAPS by isolating cells from the stromovascular fraction of human adipose tissue using collagenase digestion, and culturing these under pro-angiogenic conditions, e.g., in proprietary media EGM2-MV (Lonza) or a formulation consisting of Media 199 (GIBCO®) supplemented with glucose (10 mM), ascorbic acid (500 mM), hydrocortisone (1 uM) and human recombinant FGF-2 (0.1 nM). After sufficient cells are generated in culture, e.g. 10 days, by expansion in this media, HACAPS can be further isolated by fluorescence activated cell sorting, using specific cell surface markers listed in Table 1 including CD73.

Example 4

Adipose tissue from classically white depots has been found to contain "brite" cells. To determine whether brite cell progenitors exist within the HACAPS population, cells were grown to confluency, differentiated by addition of adipogenic cocktail, consisting of DMEM containing 10% fetal bovine serum, methylisobutyl xanthine (500 uM), dexamethasone (100 nM) and insulin (1 uM), for 3 days and a further 7 days in DMEM containing 10% fetal bovine serum and then exposed to the adenylate cyclase activator forskolin for 6 h to 2 weeks. RT-PCR analysis revealed a very large increase in the canonical brown fat cell-specific marker UCP1 (FIG. 3B), as well as other markers associated with brown cell differentiation such as CIDEA and deiodinase (DIO2; FIGS. 3C and D). A pronounced increase in UCP1 was also observed in response to the beta-adrenergic agonist isoproterenol (FIG. 3E), indicating that thermogenic capacity can be elicited in response to adrenergic stimulation, which is a physiological inducer of thermogenesis in mammals. The observed changes in mRNA resulted in a marked accumulation of UCP1 protein (FIGS. 3G and H) and induction of thermogenic oxygen consumption (FIGS. 3P and Q). Thus, these methods can be used to generate human beige/brite adipocyte progenitors through expansion of human adipose tissue vasculature, isolation and differentiation of HACAPS and exposure to adrenergic agonists or adenylate cyclase activators. Cells prepared in this manner can be re-introduced into patients for the purpose of metabolic therapy.

Example 5

The use of cells for therapeutic purposes requires the survival and functional maintenance of the cells following transplantation. To determine whether the cells generated from human explants are useful for transplantation, ex-vivo differentiated HACAPS were injected into immunocompromised mice. Four weeks later, there was a visible accumulation of adipose tissue at the site of injection (FIG. 4A-B). These represented human cells, as ascertained by their production of the human specific forms of the hormones adiponectin and leptin (FIG. 4C-D). Thus, these methods can be used to expand and adipocyte progenitors and the use of these progenitors before and/or after differentiation for adipose tissue engraftment.

Example 6

The thermoregulatory function of adipose tissue has gained much interest with the discovery that cells expressing the uncoupling protein 1 (UCP1), which generates heat by uncoupling electron transport from ATP production, are interspersed within adult human white adipose tissue (Nedergaard et al., American journal of physiology. Endocrinology and metabolism 293, E444-452 (2007); Cypess, et al., The New England journal of medicine 360, 1509-1517 (2009); van Marken Lichtenbelt et al., The New England journal of medicine 360, 1500-1508 (2009); Lidell et al., Adipocyte 3, 63-66 (2014)). The presence of these cells, referred to as "brite" ("brown-in-white") or "beige" cells, is correlated with a lean phenotype and lower metabolic disease risk (Nedergaard et al., American journal of physiology. Endocrinology and metabolism 293, E444-452 (2007); Cypess, et al., The New England journal of medicine 360, 1509-1517 (2009); van Marken Lichtenbelt et al., The New England journal of medicine 360, 1500-1508 (2009); Lidell et al., Adipocyte 3, 63-66 (2014)). Moreover, brite/beige adipose tissue increases in response to adrenergic stimulation (Wang et al., PLoS One 6, e21006 (2011)) or cold exposure (Blondin et al., J Clin Endocrinol Metab, jc20133901 (2014)), a phenomenon known as "browning," which has potential to be harnessed as a means to enhance metabolic rate and combat obesity. For this potential to be realized, it is necessary to understanding the mechanisms by which human bite/beige cells originate, proliferate, differentiate and respond to stimuli.

Methods

The following materials and methods were used in Example 6.

Materials:

Matrigel from BD biosciences; EGM-2 MV from Lonza; Anti-human UCP1 antibody from Abcam (ab10983; anti Heat Shock Protein 70 from ThermoFisher Scientific (MA3-028); Adiponectin human-specific ELISA kits from Invitrogen (KHP0041); Forskolin and Isoproterenol hydrochloride from Sigma (F3917 and 16504, respectively).

Cells.

Detailed methods for harvesting adipose tissue, culture of adipose tissue explants in Matrigel, and harvesting of single cells from explant growth are published (Rojas-Rodriguez et al., Methods in enzymology 537, 75-91 (2014)). The results shown in this example were obtained de-identified samples originating from panniculectomies/elective vascular surgeries. In brief, explants from human subcutaneous adipose tissue were cultured in EBM-2 media supplemented with endothelial growth factors (EGM-2 MV) (Lonza). EGM-2 MV includes: 0.1% hEGF; 0.04% Hydrocortisone; 0.1% GA-1000 (Gentamicin, Amphotericin-B); 5% FBS (Fetal Bovine Serum) 25 ml; 0.1% VEGF; 0.4% hFGF-B; 0.1% $R^3$-IGF-1; and 0.1% Ascorbic Acid. In indicated experiments, Dulbecco's Modified Eagles Medium supplemented with 10% fetal bovine serum ((DMEM-FBS) was used, without or with supplementation with hFGF-B, hEGF, $R^3$-IGF1 and VEGF at the concentrations used in EGM2-MV, as indicated. Single cells suspensions from capillary growth were obtained using dispase (Rojas-Rodriguez et al., Methods in enzymology 537, 75-91 (2014)). To obtain clonal populations, single cells suspensions were stained with 7-amino-actinomycin D (7-AAD) for live/dead cell identification, and sorted into individual wells of 384 well multiwell dishes using a BSL3 BD FACSAria Cell Sorter (BD Biosciences). Viable clones were passaged onto 96 well multiwell dishes. Adipogenic differentiation was induced at days 2 after confluence, by addition of DMEM-FBS, 0.5 mM 3-isobutyl-1-methylxanthine, 1 µM dexamethasone, and 1 µg/ml insulin (MDI). 72 hr later, the differentiation medium was replaced by DMEM-FBS, which was replaced every 48 hours until analysis. Oxygen consumption and mitochondrial parameters were obtained using the XF24 Extracellular Flux Analyzer equipped with a FluxPak mini kit (#100867-100) from Seahorse Biosciences.

Mice.

NOD-scid IL2rgamma null mice from Jackson Laboratories (NSG) (Brehm et al., Blood 119, 2778-2788 (2012)) were injected subcutaneously with cells suspended in Matrigel. After 4-6 weeks, animals were sacrificed and tissues were removed for further study.

Affymetrix Arrays.

Total RNA was isolated using TRIzol. Affymetrix protocols were followed for the preparation of cRNA, which was hybridized to HG-U133v2 Chips. Raw expression data collected from an Affymetrix HP GeneArrayScanner was normalized across all data sets using the RMA algorithm. A linear model approach (Smyth et al., Statistical applications in genetics and molecular biology 3, Article3 (2004)) was used to determine differentially expressed genes. Derived p-values were adjusted for multiple testing using the Benjamin & Hochberg method (Benjamin et al., Journal of the Royal Stataistical Society. Series B 57, 289-300 (1995)). Statistical significance was defined as being differentially expressed with an adjusted p-value of less than 0.05

Results

Lineage-tracing studies in mice have demonstrated that adipocyte progenitors reside within the walls of adipose tissue capillaries (Han et al., Development 138, 5027-5037 (2011); Bouloumie et al., Ann Endocrinol (Paris) 63, 91-95 (2002); Tang et al., Science 322, 583-586 (2008); Gupta et al., Cell metabolism 15, 230-239 (2012)). Moreover, during embryonic development adipocytes emerge from preformed vascular networks. These findings suggest that proliferation of adipocyte and vascular progenitors may be interdependent, insuring that adipose tissue expansion is accompanied by appropriate vascular support. To determine whether human adipocyte progenitors indeed proliferate in association with adipose tissue capillaries we used an in-vitro system (Rojas-Rodriguez et al., (2014) supra) in which human adipose tissue explants cultured in hydrogels under pro-angiogenic conditions produce capillary networks that resemble the tissue vasculature (Gealekman et al., Circulation 123, 186-194 (2011); Tran et al., Cell Metab 15, 222-229 (2012)). This assay is based on the well-established aorta ring assay, which has shown that microvessels formed in vitro are composed of the same cell types that operate in vivo (Baker et al., Nature protocols 7, 89-104 (2012)).

To determine whether adipocyte progenitors reside within capillary networks, explants were cultured in EGM-2 MV, a proprietary medium optimized for angiogenic growth. As seen previously, cells migrating from the explant extended numerous processes into the gel, and proliferated over time forming aligned, elongated cells and numerous branches (FIG. 1A). These cells form tight junctions and are associated with perivascular cells expressing smooth muscle actin (Gealekman et al., Circulation 123, 186-194 (2011); Tran et al., Cell Metab 15, 222-229 (2012)). Upon exposure to the classical adipogenic cocktail of 3-isobutyl-1-methylxanthine, dexamethasone and insulin (MDI), cells associated with capillary networks accumulated lipid droplets and migrated away from the branches (FIG. 1A, arrows). This was accompanied by induction of classical adipocyte markers, which were virtually undetectable prior to differentiation (FIG. 1B). To verify that the proliferation of adipocyte progenitor cells was indeed dependent on the pro-angiogenic properties of EGM-2 MV, explants were also cultured in DMEM supplemented with 10% fetal bovine serum. No cell proliferation was seen from these explants (FIG. 1C, top panels). However, addition of angiogenic factors (VEGF, hFGF-2, IGF1 and hEGF) stimulated the formation of branched structures characteristic of capillary networks (FIG. 1C, middle panels), and the differentiation of adipocytes within these networks. Culture in EGM-2 MV resulted in the maximal growth of capillary networks, consistent with its highly selected pro-angiogenic properties, and the largest number of differentiated cells (FIG. 1C, bottom panels, and FIG. 1D). Thus, proliferation of human adipocyte progenitors occurs in conjunction with adipose tissue vascular growth and, as such, is absolutely dependent on pro-angiogenic growth factors.

To determine whether proliferation or differentiation of adipocyte progenitors depend on specific interactions within the Matrigel or on the structure of the capillary sprouts, single cell suspensions were generated by digestion of capillary networks after mechanical removal of the original explant. These cells were plated on standard tissue culture dishes, grown to confluence in EGM-2 MV and subjected to differentiation. At least 50% of cells were identifiable as adipocytes on the basis of lipid droplets that increased in size and coalesced over time (FIG. 2A). This phenotype was accompanied by induction of adipocyte genes (FIG. 2B). To determine whether adipocyte progenitors are capable of autonomous growth and differentiation, live single cells (FIGS. 2D, E), the vast majority of which were CD45− (FIG. 2F), were individually sorted into single wells of 384 well plates. Approximately 10% of sorted cells survived and could be further passaged into 96 well multiwell plates; of these, approximately 75% underwent adipogenic differentiation, as determined both by the presence of lipid droplets (FIGS. 2G-J), and the secretion of adiponectin into the culture medium (FIG. 2K). Thus, human adipocyte progenitors isolated from growing microvessels can be clonally expanded and undergo adipocyte differentiation in response to classical adipogenic stimuli.

Adipocytes formed from angiogenic sprouts displayed diverse morphologies, suggesting that they may belong to different lineages. The key feature distinguishing brite/beige from brown adipocytes is that thermogenic genes are expressed only in response to adrenergic stimulation (Harms and Seale, Nat Med 19, 1252-1263 (2013)). To determine whether cells isolated from microvessels included brite/beige adipocyte progenitors, cells were differentiated and subsequently exposed to the adenylate cyclase activator forskolin for 6 hours to 2 weeks (FIG. 3A), or to the beta-adrenergic agonist isoproterenol for 6 hours (FIG. 3B). UCP1 message was virtually undetectable before and after adipogenic differentiation, but increased rapidly in response to forskolin, and remained elevated on chronic exposure to the drug (FIG. 3C, note log scale). In addition to UCP1, canonical brown cell markers CIDE-A and deiodinase-2 were induced in response to stimulation (FIGS. 3D, E). An acute increase in UCP1 mRNA was also seen in response to isoproterenol (FIG. 3F), demonstrating that a browning can be induced by physiologically relevant stimuli.

Immunofluorescence with anti-UCP1 antibodies confirmed that the increase in message levels translated into an increase in protein (FIGS. 3G, H). Some cells containing no detectable UCP1 signal (FIG. 3I) were also found interspersed amongst UCP1 expressing cells. Interestingly, mitochondria in these cells, identified by staining with mitochondrial-specific Hsp70, were linear and relatively sparse, while mitochondria were rounded, dense and more abundant in cells expressing UCP1 (FIG. 3J). UCP1 co-localized extensively with the mitochondrial marker (FIG. 3K), resembling brown adipocyte mitochondria (Cousin et al., Journal of cell science 103 (Pt 4), 931-942 (1992)). In addition to changes in mitochondrial structure, a remodeling of large lipid droplets into numerous small lipid droplets was observed upon exposure to forskolin (FIG. 3L). This morphological change was accompanied by a large increase in perilipin-1 mRNA (FIG. 3M). In addition, the levels of FABP4 and GLUT4, which are involved in uptake of lipids and glucose, are also increased (FIG. 3N, O), potentially reflecting increased fuel utilization. To determine whether the induction of UCP1 was indeed accompanied by functional changes in fuel utilization, oxygen consumption was measured using a Seahorse analyzer (FIG. 3P, Q). Forskolin treatment resulted in enhanced basal and FCCP-uncoupled oxygen consumption (FIG. 3P), and analysis of mitochondrial parameters (FIG. 3Q) revealed decreased ATP-production linked oxygen consumption and enhanced proton leakage, which would be expected to occur as a consequence of UCP1 mediated uncoupling. Further analysis revealed that expression of leptin decreased and expression of adiponectin increased significantly in response to forskolin (FIG. 3R, S), consistent with in-vivo data showing reduced circulating leptin, and increased adiponectin, in mice with browning induced by beta-3 adrenergic agonists (Zhang et al., Biochim Biophys Acta 1584, 115-122 (2002)). Taken together, these results suggest that brite/beige cells differentiated from capillary precursors mimic the physiological responsiveness to adrenergic stimuli displayed by brite/beige adipocytes in-vivo.

To investigate whether adipocytes formed from human capillary networks survive and display functional activity in an in vivo setting, cells were expanded into 150 mm tissue culture plates, differentiated (FIG. 5A), and after 20 days recovered from the plates using trypsin-collagenase digestion (FIG. 5B). Cell suspensions (approximately $10^7$ cells per mouse) were then mixed with cold Matrigel, and injected into the dorsal region NOD scid IL2rγ null (NSG) mice (Blood 119, 2778-2788 (2012)). Three weeks following injection, animals were bled, sacrificed, and the sites of injection examined. In control mice receiving only Matrigel, solidified remains of the hydrogel were seen in the dorsal region under the skin (FIGS. 5C, D). Numerous cells infiltrating the Matrigel were detected using Hoechst (FIG. 5E), several of which contained lipid droplets (FIG. 5F), consistent with the finding that Matrigel by itself can induce formation of adipose tissue (Kawaguchi et al., Proceedings of the National Academy of Sciences of the United States of America 95, 1062-1066 (1998)). In mice receiving human cells, the formation of a vascularized, adipose tissue structure adjacent to the interscapular fat of the mouse was observed (FIGS. 5G,H). This structure was heavily infiltrated with cells (FIG. 5I), many of which were adipocytes (FIG. 5J). To verify that human adipocytes were present, the presence of human adiponectin was tested in serum from the injected mice. Human adiponectin was undetectable in mice receiving Matrigel, but clearly detected in animals receiving cells (FIG. 5K), unequivocally confirming that adipocytes were viable and integrated into the mouse circulation.

To examine whether brite/beige adipocytes would affect metabolism, similar experiments were conducted with cells treated with forskolin for 10 days prior to injection. To determine whether the levels of functional brown adipocyte markers in brite/beige adipocytes implanted into the mice were similar to those in human brite/beige adipose tissue, perivascular adipose tissue surrounding the carotid artery was collected from four patients undergoing elective surgery. While the variability in UCP1 and deiodinase-2 expression is large both among capillary-derived adipocytes from different individuals, and among perivascular tissue samples, the values were comparable (FIGS. 5L,M). Two weeks following injection, mice were fasted and subjected to glucose tolerance tests. Mice injected with brite/beige adipocytes displayed enhanced glucose utilization, as evidenced by lower fasting glucose (FIG. 5N) and a more rapid glucose disposal rate (FIGS. 5O, P). To the present inventors' knowledge, these experiments are first to observe an improvement in glucose metabolism directly attributable to the presence of transplanted human brite/beige cells.

To determine whether the improvement in glucose tolerance seen in mice harboring human beige/brite cells was related to a thermogenic phenotype, mice were subcutaneously implanted at the flank with Thermochron iButton temperature loggers, which have a resolution of 0.025° C., set to record at 30 min intervals. This method was very sensitive, as even small fluctuations in core temperature associated with the onset of light/dark periods were detected (FIG. 5Q). Mice harboring beige/brite cells did not differ significantly from Matrigel controls in their basal body temperature, in the rate of temperature drop upon cold exposure, or in their adaptation to cold (FIG. 5Q).

It remains possible that local thermogenic effects, undetectable by whole body temperature measurements might contribute to improved glucose disposal in mice implanted with human brite/beige cells; nevertheless, improvement in metabolic parameters attributable to factors secreted from brown adipose and independent of thermogenesis has been reported (Wang et al., Nature medicine 20, 1436-1443 (2014)). To examine whether the metabolic benefits of human beige/brite adipocytes may be also attributable to secreted factors, global gene expression analysis was conducted on cells before and after forskolin-induced browning. Strikingly, amongst the 20 most highly induced genes in response to forskolin were interleukin IL-33, the proprotein-convertase subtilisin/kexin type-1 (PCSK1) and its substrate proenkephalin (PENK) (FIG. 5Q), which were also expressed in perivascular adipose tissue samples (FIGS. 5R-U). Mutations and polymorphisms in PCSK1 are strongly associated with human obesity (Jackson et al., Nature genetics 16, 303-306 (1997); Benzinou et al., Nature genetics 40, 943-945 (2008); Wen et al., Nature genetics 44, 307-311 (2012)) and IL33 has been shown to decrease adiposity, mitigate atherosclerosis and be necessary for normal glucose homeostasis (Miller et al., Circ Res. 2010 Sep. 3; 107(5):650-8). Similar to UCP1 (FIG. 5L), and in contrast to adiponectin (FIG. 5U), mRNA levels of IL-33, PENK and PCSK1 were increased in response to forskolin treatment, rather than in response to adipogenic differentiation, suggesting that their expression is linked to the activation of beige/brite adipocytes.

In summary, the present data indicate that human adipocyte progenitor cells are associated with adipose tissue vasculature, and proliferate in conjunction with the vasculature in response to pro-angiogenic stimuli. These cells display the cardinal functional feature of brite/beige adipocytes, which is the induction of functional brown adipocyte markers in response to adrenergic stimulation. Moreover, these cells confer improved glucose homeostasis when implanted into mice, providing a rationale for their potential therapeutic use.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of making a population of brite adipose cells from Human Adipose Capillary Progenitor Cells (HACAPS), the method comprising: providing primary adipose cells or tissue from a subject, and
   (i) culturing the primary cells or tissue in the presence of pro-angiogenic factors sufficient to induce growth of a population of cells comprising capillary cells, wherein the pro-angiogenic factors comprise human recombinant FGF-2 in combination with one or more of VEGF, IGF1, and EGF, and then
   (ii) isolating single cells from the population of cells to form a population of cells enriched for HACAPS, and
   (iii) maintaining the HACAPS in culture in the presence of adenylate cyclase activators or adrenergic agonists to induce differentiation of the HACAPS into brite adipose cells.

2. The method of claim 1, wherein isolating single cells from the capillary cells comprises subjecting the capillary cells to protease digestion to isolate the HACAPS.

3. The method of claim 1, further comprising maintaining the HACAPS in culture for a time and under conditions sufficient for the cells to proliferate.

4. The method of claim 1, wherein the subject is a mammal.

5. The method of claim 1, comprising maintaining the HACAPS in culture in the presence of an adenylate cyclase activator.

6. The method of claim 5, where in the adenylate cyclase activator is forskolin.

7. The method of claim 1, comprising maintaining the HACAPS in culture in the presence of an adrenergic agonist.

* * * * *

UNITED STATES PATENT AND TRADEMARK OFFICE
CERTIFICATE OF CORRECTION

PATENT NO. : 10,093,902 B2
APPLICATION NO. : 14/660381
DATED : October 9, 2018
INVENTOR(S) : Silvia Corvera Page 1 of 1

It is certified that error appears in the above-identified patent and that said Letters Patent is hereby corrected as shown below:

On the Title Page

Column 1 (Other Publications), Line 9, delete "PCK1" and insert --PCSK1--.

Signed and Sealed this
Fourth Day of December, 2018

Andrei Iancu
*Director of the United States Patent and Trademark Office*